(12) United States Patent
Michl et al.

(10) Patent No.: US 7,883,888 B2
(45) Date of Patent: Feb. 8, 2011

(54) PEPTIDES SELECTIVELY LETHAL TO MALIGNANT AND TRANSFORMED MAMMALIAN CELLS

(75) Inventors: Josef Michl, Little Neck, NY (US); Jesko Koehnke, Oldenburg (DE); Matthew R. Pincus, Brooklyn, NY (US)

(73) Assignee: The Research Foundation —The State University of New York, Albany, NY (US)

( * ) Notice: Subject to any disclaimer, the term of this patent is extended or adjusted under 35 U.S.C. 154(b) by 648 days.

(21) Appl. No.: 10/549,048

(22) PCT Filed: Jan. 13, 2004

(86) PCT No.: PCT/US2004/000684

§ 371 (c)(1),
(2), (4) Date: Dec. 13, 2006

(87) PCT Pub. No.: WO2004/081030

PCT Pub. Date: Sep. 23, 2004

(65) Prior Publication Data

US 2008/0070853 A1 Mar. 20, 2008

Related U.S. Application Data

(63) Continuation-in-part of application No. 10/386,737, filed on Mar. 12, 2003, now abandoned, and a continuation-in-part of application No. 09/827,683, filed on Apr. 5, 2001, now abandoned.

(60) Provisional application No. 60/363,785, filed on Mar. 12, 2002, provisional application No. 60/195,102, filed on Apr. 5, 2000.

(51) Int. Cl.
*C12N 15/00* (2006.01)
(52) U.S. Cl. .................................. 435/320.1
(58) Field of Classification Search ............... 435/320.1
See application file for complete search history.

(56) References Cited

U.S. PATENT DOCUMENTS 5,550,023 A * 8/1996 Kinzler et al. ............... 435/7.1

FOREIGN PATENT DOCUMENTS

WO    WO 97/17090    * 5/1997

OTHER PUBLICATIONS

Kanovsky et al., "Peptides from The amino terminal mdm-2-Binding domain of p53, Designed from conformational analysis, are selectively cytotoxic analysis, are selectively cytotoxic to transformed cells", Oct. 23, 2001.
Kozarsky et al., "Gene Therapy: adenovirus vectors", 1993.
Uchida et al., "Clinical significance of p53, MDM2 and bcl-2 expression in transitional Cell Carcinoma of the Bladder", Nov. 30, 2001.
Chen, Mack et al., 1997"Persistance in muscle of an adenoviral vector that lacks all viralgenes"Proc. Natl. Acad. Sci. USA 94 (4): 1645-1650.
Crouzet J, L. Naudin et al., 1997, "Recombinational construction in *Escherichia coli* of infectious adenoviralgenomes"Proc. Natl. Acad. Sci. USA 94 (4): 1414-1419.
Goodbourn, S. ,Didcock, L. & Randall, R. E. (2000). Interferons : cell signaling, immune modulation, antiviral responses and viruscountermeasures.Journal of General Vivology 81, 2341-2365.
Israel, B.F. et al. J. Virol. 2001,75 (11): 5215-5221: Enhancement of adenovirus vector entry into CD70- positive B-cell lines by using a bispecific CD70- adenovirus fiber antibody.
Kanovsky M, Raffo A, Drew L, Rosal R, Do T, Friedman FK, Rubinstein P, Visser J, Robinson R, Brandt-Rauf PW, Michl J, Fine RL, Pincus MR;Proc Natl Acad SciU S A. Oct. 23, 2001; 98 (22):12438-43 : Peptides from the amino terminal mdm-2- binding domain of p53, designed fromconformational analysis, are selectively cytotoxic to transformed cells.
Kozarsky, KF and Wilson JM (1993). Gene Therapy : Adenovirus Vectros. Curr. Opin. Genet. Dev. 3,499-503.
Lusky, Christ et al. ,1998 In vitro and in vivo biology of recombinant adenovirus vectors with E1,E1/E2A, or E1/E4 deleted: Virol. 72 (3): 2022-3.
Mathias, P., Galleno, M. & Nemerow, G. R. (1998). Interactions of soluble recombinant integrin ayss5 with humanadenoviruses. Journal of General virology 75,3365-3374.
Meredith, J. E. , Jr, Winitz, S. , Lewis, J. M. , Hess, S. , Ren, X. D. , Renshaw, M. W. & Schwartz, M. A. (1996). The regulation of growth and intracellular signaling by integrins. Endocrinology Reviews 17,207-220.
Michl J. DJ Ohlbaum, SC Silverstein, 1976.2-Deoxyglucose selectively inhibits Fc and complement receptor-mediated phagocytosis in mouse peritoneal macrophages.
Morral, O'Neal et al., 1999"Administration of helper-dependent adenoviral vectors and sequential delivery of different vector serotype for long-term liver-directed gene transfer inbaboons."Proc. Natl. Acad. Sci. USA96 (22):12816-12821.

(Continued)

*Primary Examiner*—Brian Whiteman
(74) *Attorney, Agent, or Firm*—Dilworth & Barrese, LLP

(57) ABSTRACT

The present invention provides peptides corresponding to all or a portion of amino acid residues 12-26 of human p53 protein, which peptides are lethal to malignant or transformed cells when fused to a membrane-penetrating leader sequence. The subject peptides are thus useful in treating neoplastic disease in an animal, preferably a human. Also provided are pharmaceutical compositions comprising the subject peptides admixed with a pharmaceutical acceptable carrier. Methods of treating neoplastic disease in a patient by administering a subject peptide fused at its carboxy terminal end to a membrane penetrating leader sequence are also provided. The present invention also provides replication incompetent Adenovirus (AdV) vectors comprising a promoter sequence operably linked to a nucleotide sequence encoding a subject peptide. Methods of selectively killing cancer cells in a subject by administering a therapeutically effective amount of a subject AdV vector are also provided by the present invention.

6 Claims, 13 Drawing Sheets

OTHER PUBLICATIONS

Russel, W. C. (2000) Update on adenovirus and its vectors. Journal of General Virology, vol. 81 2573-2604 25. Saiki, R.K., Scharf, S. J.,Faloona, F., Mullis, K.EN., Horn, Gg T., Erlich, Ho A. andAmheim, N. (1985) Science, 230,1350.

Stow, N. D. , 1981, "Cloning a DNA fragment from the left-hand terminus of the adenovirus type 2 genome and its use in site-directedmutagenesis"J. Virol. 37:171-180.

Uchida T. , Minei S. , Gao, J. , Wang C. , Satoh T. , Baba S. (2002) Clinical significanceof p53, MDM2 andbcl-2 expression in transitional cell carcinoma of the bladder. Oncology Reports 9: 253-259.

Wickham,T. J. ,Segal, D. M., Roelvink, P.W., Carrion, M. E. , Lizonova, A., Lee,G. M.and EXovesdi, I.; J. Virol. 1996,70 :6831-6838 : Targeted adenovirus gene transfer to endothelial and smooth muscle cells by using bispecific antibodies.

Yang, Y. , Li, Q., Ertl, H. C. J. and Wilson, J. M.; J. Virol. 1995,69 : 2004-2015: Cellular and humoral immune responses to viral antigens create barriers to lung directed gene therapy with recombinant adenoviruses.

Yang, Y. , Nunes, F. A. , Berencsi, K. , Furth, E. F., Gonczol, E. and Wilson, J. M.; Proc. Natl. Acad. Sci. 1994,91 : 4407-4411 : Cellular immunity to viral antigens limits El-deletedadenoviruses for gene therapy.

\* cited by examiner

FIG. 3

5'-ATCCGGTACCAA▓▓GAGACCTTTTCTGACCTCTGGAAACTCCTC▓▓AAGCGGCCGCACTC-3'
            E   T   F   S   D   L   W   K   L   L
           Glu thr phe ser asp leu trp lys leu leu
3'-TAGGCCATGGTTTAC'CTCTGGAAAAGACTGGAGACCTTTGAGGAG'ATCTTCGCCGGCGTGAG-5'

```
                  CAAT                                              TATA       3'end of        Putative
                                                                               CMV promoter   transcriptional start
1261 TTGACGCAAA TGGGCGGTAG GCGTGTACGG TGGGAGGTCT ATATAAGCAG AGCTCTCTGG CTAACTAGAG
                                           T7 promoter/priming site
1331 AACCCACTGC TTACTGGCTT ATCGAAATTA ATACGACTCA CTATAGGGAG ACCCAAGCTG GCTAGTTAAG
              1414   attB 1                                       attB 2       3657
1401 CTATCAACAA GTTTGTACAA AAAAGC AGG CTN ___ ___ ___ NAC CCA GCT TTC TTG TAC AAA
     GATAGTTGTT CAAACATGTT TTTTCG TCC GAN ___GENE___ NTG GGT CGA AAG AAC ATG TTT
                                                        Pro Ala Phe Leu Tyr Lys
                                              V5 epitope       V5(C-term) reverse priming site
3667 GTG GTT GAT CTA GAG GCC CCG CGG TTC GAA GGT AAG CCT ATC CCT AAC CCT CTC CTC
     CAC CAA
     Val Val Asp Leu Glu Gly Pro Arg Phe Glu Gly Lys Pro Ile Pro Asn Pro Leu Leu 3724 GGT CTC GAT TCT ACG CGT ACC GGT TAG TAA TGA GTTT AAACGGGGGA GGCTAACTGA
     Gly Leu Asp Ser Thr Arg Thr Gly * * ***
```

FIG. 12B
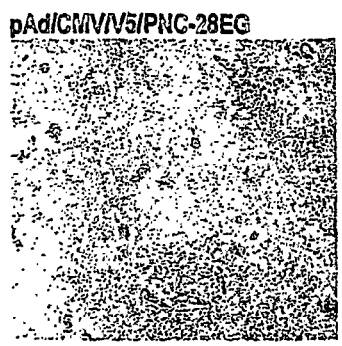 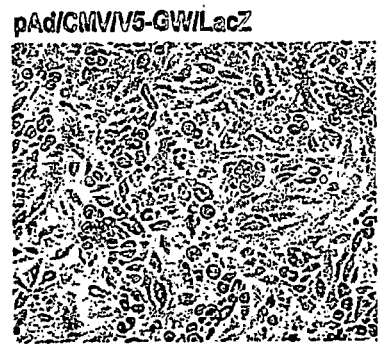 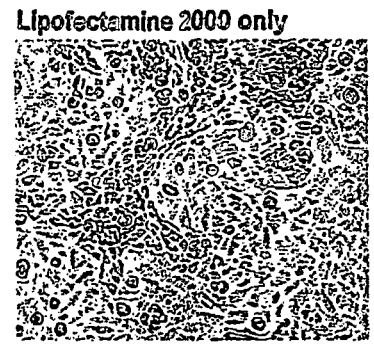

PEPTIDES SELECTIVELY LETHAL TO MALIGNANT AND TRANSFORMED MAMMALIAN CELLS

CROSS REFERENCE TO RELATED APPLICATIONS

This application is a 371 of application No. PCT/US04/000684, filed Jan. 13, 2004 and a continuation-in-part application of application Ser. No. 10/386,737 (now Abandoned), filed Mar. 12, 2003. U.S. Ser. No. 10/386,737 claims the benefit of U.S. Provisional Application No. 60/363,785, filed Mar. 12, 2002, and is a continuation-in-part application of application Ser. No. 09/827,683 (now Abandoned), filed Apr. 5, 2001. U.S. Ser. No. 09/827,683 claims the benefit of U.S. Provisional Application Ser. No. 60/195,102, filed Apr. 5, 2000.

BACKGROUND OF THE INVENTION

This invention relates to therapeutic modalities for treatment of neoplastic disease. More specifically, this invention involves synthetic peptides that selectively destroy malignant and transformed cells, and a method for treatment of neoplastic disease based thereon. The present invention also relates to viral therapy for cancer.

The p53 protein is a vital regulator of the cell cycle. It blocks the oncogenic effects of a number of oncogene proteins that induce mitosis, in part by blocking transcription of proteins that induce mitosis and by inducing the transcription of proteins that block mitosis, and promote apoptosis. Absence of the p53 protein is associated with cell transformation and malignant disease. Haffner, R & Oren, M. (1995) *Curr. Opin. Genet. Dev.* 5: 84-90.

The p53 protein molecule consists of 393 amino acids. It includes domains that bind to specific sequences of DNA in a DNA-binding domain that consists of residues 93-313. The crystal structure of this region has been determined by x-ray crystallography. Residues 312-393 are involved in the formation of homotetramers of the p53 protein. Residues 1-93 are involved in regulation of the activity and half life of the p53 protein.

The p53 protein binds to another important regulatory protein, the MDM-2 protein. The MDM-gene that encodes the MDM-2 protein is a known oncogene. The MDM-2 protein forms a complex with the p53 protein, which results in the degradation of the p53 protein by a ubiquination pathway. The p53 protein binds to MDM-2 protein using an amino acid sequence that includes residues 14-22 of the p53 protein, which are invariant. The entire MDM-2 protein binding domain of the p53 protein spans residues 12-26. Haffner, R & Oren, M. (1995) *Curr. Opin. Genet. Dev.* 5: 84-90.

Considering that the MDM-2 protein is the expression product of a known oncogene, it is not surprising that MDM-2 protein is a very important regulatory protein. Moreover, overexpression or amplification of MDM-2 protein has been found in 40-60% of human malignancies, including 50% of human breast tumors. It has been suggested that formation of a complex between the p53 protein and the MDM-2 protein may result in the inhibition of transcription activity of the p53 protein, and thus the anti-tumor effect of the molecule by blocking of an activation domain of the p53 protein, or of a DNA binding site within it. More generally, these and other experimental observations have been interpreted as suggesting that the anti-tumor effect of the p53 protein might be enhanced by peptides capable of interfering with the binding of the MDM-2 protein to the p53 protein. Indeed, a number of investigators have suggested that the MDM-2/p53 complex might be a target for rational drug design. See, e.g., Christine Wasylyk et al., "p53 Mediated Death of Cells Overexpressing MDM2 by an Inhibitor of MDM2 Interaction with p53", *Oncogene,* 18, 1921-34 (1999), and U.S. Pat. No. 5,770,377 to Picksley et al.

The ability of the adenovirus to infect a broad spectrum of cells and its high infection efficiency has made it a prominent candidate for cancer therapy (Russell, 2000). The adenovirus consists of an icosahedral capsid. The capsid, which encloses the viral genome, is composed of three major proteins: a hexon, a penton base, and a protein called knobbed fibre. In addition, several minor proteins, VI, VIII, IX, IIIa and IVa2 and a virus-encoded protease are also present. The viral genome is a linear, double-stranded DNA with a terminal protein attached covalently to the 5' termini, which have long terminal repeats (LTRs). The DNA is also associated with protein VII and a peptide known as mu (Russell, 2000). The adenoviral genome can be subdivided into three functional categories: the early genes, which encode for the E1A, E1B, E2, E3 and E4 proteins, the delayed genes and the single major late unit. DNA replication, viral gene transcription, host cell immune suppression and inhibition of host cell apoptosis can be attributed to the early gene products. The products of the late genes are required for virus assembly (Wang et al., 2000).

The infectious cycle of the Adenovirus can be defined in an early phase and a late phase. The early phase covers the entry of the virus into the host cell, followed by the passage of the viral genome into the nucleus and selective transcription and translation of the early genes Russell, 2000). In these early events the virus takes over the functions of the host cell in order to facilitate the replication of the viral DNA, which leads to the translation of the late genes. A key factor in cell tropism is receptor recognition. The protein knobbed fibre binds with high affinity to a cell surface receptor known as Coxsackie Adenovirus Receptor (CAR). Infection of cells is first initiated by the binding of the knob fibre to CAR. Internalization of the virus involves the additional binding of the penton base to surface integrins—proteins which are involved with the extracellular matrix in cell adhesion, cell-cell junctions and other cell-cell related phenomena (Mathias et al., 1998; Meredith et al., 1996). A number of signaling pathways are then induced that facilitate the clathrin-mediated endocytosis of the viral particle. Endocytosis involves the invagination of the viral particle followed by the pinching off the plasma membrane resulting in the development of endocytic vesicles. The virus-encoded protease then disrupts the viral capsid by degradation of the structural protein VI. The virus is then transported into the nuclear membrane, where the genome enters into the nucleus leading to initial transcription. It is believed that the viral genome is able to access the host nucleus through the help of the cellular protein p32. p32 is found primarily in the mitochrondria, but is also present in the nucleus. The protein acts as an intracellular shuttle between the mitochondria and nucleus. It appears that the virus is able to take over this intracellular shuttle system in order to gain access to the nucleus (Russell, 2000).

Low morbidity and high-level transgene expression have made adenovirus a very attractive vector in functional studies. However, the supremacy of the immune response in vivo has been a limiting factor in the practical development of vectors. The duration of the transgene expression is limited in vivo to a large extent by the host's anti-adenoviral immune response toward the infected cell (Yang et al., 1996). Epithelial cells for example are able to release antimicrobial peptides that inhibit adenoviral infection (Gropp et al. 1999). Other defense mechanisms include the release of cellular proteins known as interferons, upon early infection. Interferons activate the cellular Jak/STAT pathway; which results in the activation of Interferon-response elements that regulate the transcription of a range of gene products that can eliminate the infected cells and protect healthy cells from infection (Goodbourn et al., 2000). T-cell recognition of viral antigens presented on the surface of the infected cells in context of MHC Class I antigens can result in the transfer of perforin from cytotoxic T-cells and the lysis of infected cells. Viral activity can also invoke apoptotic pathways leading to programmed cell death. Particularly in cancer therapy, where the goal is to eliminate all transformed cells, the activation of the immune response is a desired effect.

The tumor suppressor p53 plays a primary role in apoptosis and cell cycle arrest (Alberts et al., 2002). This protein regulates the transcription of anti-proliferative proteins such as Bax. Bax stimulates the release of cytochrome c from mitochondria, which binds to the adaptor protein Apaf-1 and the whole complex then activates procaspases leading to cell death (Alberts et al., 2002). p53 is regulated by the oncoprotein murine double minute 2, mdm2. Mdm2 is able to form complexes with p53 protein leading to its ubiquitination and its degradation by proteasomes (Uchida et al., 2002). p53 provides protection from dangerous events such as uncontrolled cell proliferation and mutations that may arise in the cell. A defective p53 gene can have numerous adverse consequences for the cell. Cells defective in p53 or containing mutated p53 are able to circumvent apoptosis and continue their proliferation. DNA damages within these cells accumulate with each new division, while the cell is unable to repair them. Thus, loss of p53 function is closely related to the development of cancer. Loss of p53 function allows mutant cells to continue through the cell cycle, to bypass apoptosis and the accumulation of cancer-promoting mutations as they divide (Alberts et al., 2002).

Mutations in the p53 gene and its relation to the development of a wide variety of human tumors have prompted the development of vectors incorporating wild-type p53. Such vectors have been tested successfully in vitro and in vivo in anaplastic thyroid cancer, human malignant gliomas and breast cancer with success (Russell, 2000).

In addition to providing peptides which selectively kill malignant or transformed cells, the present invention provides adenoviral vectors (AdV) that incorporate a transgene, which codes for such peptides. Administration of such vectors to malignant and transformed cells results in death of such cells. The subject AdV expression vehicles are especially useful for their anti-proliferative properties in treating different neoplastic diseases including pancreatic cancer.

SUMMARY OF THE INVENTION

The present invention provides a peptide comprising at least about six contiguous amino acids of the amino acid sequence: PPLSQETFSDLWKLL (SEQ ID NO:1), or an analog or derivative thereof, wherein said peptide or analog or derivative thereof is fused to a membrane-penetrating leader sequence and is selectively lethal to malignant or transformed cells.

Examples of such peptides include PPLSQETFSDL-WKLL (SEQ ID NO:1) or an analog or derivative thereof, PPLSQETFS (SEQ ID NO:2) or an analog or derivative thereof and ETFSDLWKLL (SEQ ID NO:3) or an analog or derivative thereof. In order to be transported across a cell membrane and selectively kill a malignant or transformed cell, the leader sequence is preferably positioned at the carboxyl terminal end of the peptide, analog, or derivative thereof. Preferably, the leader sequence comprises predominantly positively charged amino acid residues. Examples of leader sequences which may be used in accordance with the present invention include but are not limited to penetratin, $Arg_8$, TAT of HIV1, D-TAT, R-TAT, SV40-NLS, nucleoplasmin-NLS, HIV REV (34-50), FHV coat (35-49), BMV GAG (7-25), HTLV-II REX (4-16), CCMV GAG (7-25), P22N (14-30), Lambda N (1-22), Delta N (12-29), yeast PRP6, human U2AF, human C-FOS (139-164), human C-JUN (252-279), yeast GCN4, and p-vec. Preferably, the leader sequence is the penetratin sequence from antennapedia protein having the amino acid sequence KKWKMRRNQFWVKVQRG (SEQ ID NO:4).

Pharmaceutical compositions comprising at least one of the subject peptides admixed with a pharmaceutically acceptable carrier are also provided. In addition, methods for treating neoplastic disease in a subject i.e., selectively killing malignant or neoplastic cells in a subject, are provided. In one embodiment, the method comprises administering to the subject, a therapeutically effective amount of a peptide comprising at least about six contiguous amino acids of the amino acid sequence: PPLSQETFSDLWKLL (SEQ ID NO:1), or an analog or derivative thereof, wherein said peptide or analog or derivative thereof is fused at its carboxy terminal end to a membrane-penetrating leader sequence and is selectively lethal to malignant or transformed cells. In another embodiment, the method comprises administering to the subject, a therapeutically effective amount of at least one peptide having the sequence set forth in SEQ ID NO:1, SEQ ID NO:2, or SEQ ID NO:3, or an analog or derivative thereof, wherein a membrane-penetrating leader sequence is fused to the carboxy terminal end of the peptide, analog, or derivative thereof.

The present invention also provides replication incompetent Adenovirus (AdV) vectors comprising a promoter operably linked to a nucleotide sequence encoding a subject peptide. Examples of replication incompetent AdV include e.g., an AdV having the E1 and E3 genes deleted. In one embodiment, there is provided a replication incompetent AdV vector comprising a promoter operably linked to a nucleotide sequence encoding a subject peptide wherein the peptide comprises at least about six contiguous amino acids of the amino acid sequence: PPLSQETFSDLWKLL (SEQ ID NO:1), or an analog or derivative thereof. For example, a replication incompetent AdV vector comprising a promoter sequence operably linked to a nucleotide sequence encoding the amino acid sequence PPLSQTFSDLWKLL (SEQ ID NO:1) or an analog or derivative thereof is provided. In another embodiment of the present invention, there is provided a replication incompetent AdV vector comprising a promoter sequence operably linked to a nucleotide sequence encoding the amino acid sequence: PPLSQETFS (SEQ ID NO:2) or an analog or derivative thereof. In still another embodiment of the invention, there is provided a replication incompetent AdV vector comprising a promoter sequence operably linked to a nucleotide sequence encoding the amino acid sequence: ETFSDLWKLL (SEQ ID NO:3) or an analog or derivative thereof.

In another aspect of the present invention, there is provided a method of selectively killing malignant or neoplastic cells in a patient. The method comprises administering to the patient, a therapeutically effective amount of a subject replication incompetent AdV vector comprising a promoter operably linked to a nucleotide sequence encoding any of the aforementioned peptides or an analog or derivative thereof. Preferably, the malignant or neoplastic cells are pancreatic cancer cells.

BRIEF DESCRIPTION OF THE DRAWINGS

FIG. 3 shows the 62 bp DNA sequence of PNC-28EG as shown in SEQ. ID NO. 30. Both the initiation codon and stop codon are highlighted. The sequence encoding the subject peptide is highlighted in italics as shown in SEQ. ID NO. 31. Beneath each codon of the DNA sequence is the corresponding amino acid.

FIG. 5 is a nucleotide sequence and restriction map of the pCR2.1 Topo vector as shown in SEQ. ID NO. 32. The label "PCR Product" indicates where the PNC-28EG is cloned in the vector. The cloned gene lies within the sequence range of the universal M13 primers which are used as sequencing primers. The vector contains the ampicillin and kanamycin resistance genes and the lacZ gene.

FIG. 9 is a map of the Ad/CMVN5-DEST vector as shown in SEQ. ID NO. 35. As also shown in the map is amino acid sequence 35 corresponding to application of the DNA sequences show in SEQ. ID NO. Q having SEQ. ID NO. 36.

FIG. 12B are photomicrographs showing BMRPA1.TUC3 cells 72 hours post transfection.

DETAILED DESCRIPTION OF THE INVENTION

Figure 1:
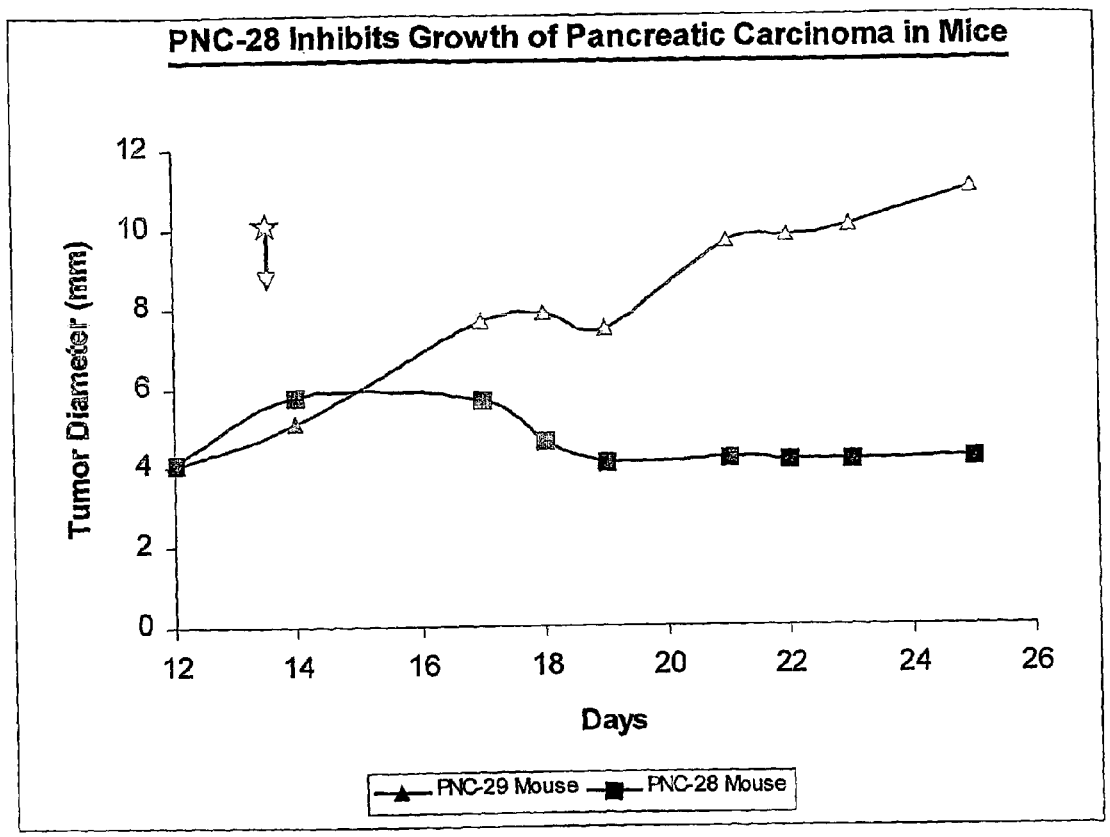
FIG. 1 graphically depicts the in vivo tumor-inhibiting effect of PNC-28 (SEQ ID NO:3 fused at its carboxy terminal end to SEQ ID NO:4) in homozygous NU/NU mice xenotransplanted with pancreatic carcinoma cells. The arrow with a star indicates the time of s.c. pump implantation on day 13 (precisely 13.5) during the tumor growth period.

In accordance with the present invention, it has been discovered that malignant and transformed cells are selectively destroyed by administration of a synthetic peptide comprising a sequence of amino acids within the p53 protein and a leader sequence as a single continuous polypeptide chain. The mechanism of action appears to be independent of the p53 protein binding to the MDM-2 protein, as the p53 peptide selectively kills transformed cells that do not produce the p53 protein at all. The p53 peptide also selectively kills malignant and transformed cells that express normal or elevated levels of the p53 protein without killing normal cells.

In accordance with the present invention, there are provided compositions comprising peptides corresponding to all or a portion of amino acid residues 12-26 of human p53. This region is known to contact the hdm-2 and mdm-2 protein and adopts an α-helical conformation when bound to either protein. When fused on the carboxy-terminal end with a membrane-penetrating leader sequence, the subject peptides selectively kill malignant and transformed human cells.

In a first aspect of the invention, there is provided a peptide comprising at least about six contiguous amino acids of the following amino acid sequence: PPLSQETFSDLWKLL (SEQ ID NO:1), wherein the peptide comprising at least about six contiguous amino acids is fused to a leader sequence. Preferably, the peptide comprises from at least about eight (8) to at least about fifteen (15) amino acid residues. In a preferred embodiment, a peptide comprising from at least about eight (8) to at least about 15 (fifteen) amino acids of the sequence set forth in SEQ ID NO:1 has the following amino acid sequence: PPLSQETFSDLWKLL (SEQ ID NO:1). In another preferred embodiment, a peptide comprising from at least about eight (8) to at least about 15 (fifteen) amino acids of the sequence set forth in SEQ ID NO:1 has the following amino acid sequence: PPLSQETFS (SEQ ID NO:2). In still another preferred embodiment, a peptide comprising from at least about eight (8) to at least about fifteen (15) amino acids of the sequence set forth in SEQ ID NO:1 has the following amino acid sequence: ETFSDLWKLL (SEQ ID NO:3).

Leader sequences which function to import the peptides of the invention into a cell may be derived from a variety of sources. Preferably, the leader sequence comprises predominantly positively charged amino acid residues since a positively charged leader sequence stabilizes the alpha helix of a subject peptide. Examples of leader sequences which may be linked to the peptides of the present invention are described in Futaki, S. et al (2001) Arginine-Rich Peptides, *J. Biol. Chem.* 276,:5836-5840, and include but are not limited to the following membrane-penetrating leader sequences (numbering of the amino acid residues making up the leader sequence of the protein is indicated parenthetically immediately after the name of the protein in many cases): penetratin (KKWKMRNQFWVKVQRG)(SEQ ID NO:4); $(Arg)_8$ or any poly-R from $(R)_4$-$(R)_{16}$; HIV-1 TAT(47-60) (YGRKKRRQRRRP-PQ)(SEQ ID NO:5); D-TAT (GRKKRRQRRRPPQ)(SEQ ID NO:6); R-TAT $G(R)_9PPQ$(SEQ ID NO:7); SV40-NLS (PKKKRKV)(SEQ ID NO:8); nucleoplasmin-NLS (KRPAAIKKAGQAKKKK)(SEQ ID NO:9); HV REV (34-50)-(TRQARRNRRRRWRERQR)(SEQ ID NO:10); FHV (35-49) coat-(RRRRNRTRRNRRRVR)(SEQ ID NO:11); BMV GAG (7-25)-(KMTRAQRRAAARRNRWTAR)(SEQ ID NO:12); HTLV-II REX 4-16-(TRRQRTRRARRNR) (SEQ ID NO:13); CCMV GAG (7-25)-(KLTRAQR-RAAARKNKRNTR)(SEQ ID NO:14); P22 N (14-30)(NA-KTRRHERRRKLAIER)(SEQ ID NO:15); LAMBDA N (1-22)(MDAQTRRRERRAEKQAQWKAAN)(SEQ ID NO:16); Phi N (12-29) (TAKTRYKARRAELIAERR)(SEQ ID NO:17); YEAST PRP6 (129-124) (TRRNKRNRIQEQL-NRK) (SEQ ID NO:18); HUMAN U2AF (SQMTRQAR-RLYV)(SEQ ID NO:19); HUMAN C-FOS (139-164) KRR-IRRERNKMAAAKSRNRRRELTDT (SEQ ID NO:20); HUMAN C-JUN (252-279) (RIKAERKRMRNRI-AASKSRKRKLERIAR)(SEQ ID NO:21); YEAST GCN4 (KRARNTEAARRSRARKLQRMKQ)(SEQ ID NO:22); KLALKLALKALKAALKLA(SEQ ID NO:23); p-vec LLI-ILRRRIRKQAKAHSK(SEQ ID NO:24). Other membrane penetrating leader sequences may also be used. Such sequences are widely available and are described e.g., in Scheller et al. (2000) *Eur. J. Biochem.* 267:6043-6049, and Elmquist et al., (2001) *Exp. Cell Res.* 269:237-244.

Preferably, the positively charged leader sequence of the penetratin leader sequence of antennapedia protein is used. This leader sequence has the following amino acid sequence: KKWKMRRNQFWVKVQRG (SEQ ID NO:4). Preferably, the leader sequence is attached to the carboxyl terminal end of the p53 peptide to enable the synthetic peptide to kill transformed and malignant cells.

Structurally related amino acid sequences may be substituted for the disclosed sequences set forth in SEQ ID NOs: 1, 2, 3, or 4 in practicing the present invention. Any of the sequences set forth in SEQ ID NOs: 1, 2 or 3, including analogues or derivatives thereof, when joined with a leader sequence, including, but not limited to the sequence set forth in SEQ ID NO: 4, will be referred to herein as either a "synthetic peptide" or "synthetic peptides." Rigid molecules that mimic the three dimensional structure of these synthetic peptides are called peptidomimetics and are also included within the scope of this invention. Alpha helix stabilizing amino acid residues at either or both the amino or carboxyl terminal ends of the p53 peptide may be added to stabilize the alpha helical conformation which is known to be the conformation of this region of the p53 protein when it binds to the MDM-2 protein. Examples of alpha helical stabilizing amino acids include Leu, Glu (especially on the amino terminal of the helix), Met and Phe.

Amino acid insertional derivatives of the peptides of the present invention include amino and/or carboxyl terminal fusions as well as intra-sequence insertions of single or multiple amino acids. Insertional amino acid sequence variants are those in which one or more amino acid residues are introduced into a predetermined site in a subject peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala (A) | Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Pro |
| His (H) | Asn; Gln |
| Ile (I) | Leu; Val |
| Leu (L) | Ile; Val |
| Lys (K) | Arg; Gln; Glu |
| Met (M) | Leu; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

When the synthetic peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "fragment", "portion" and "like molecule" refer to a subject peptide having the amino acid sequence as set forth in SEQ ID NOs:1, 2, 3, or 4, having an amino acid substitution, insertion, addition, or deletion, as long as said derivative, analogue, fragment, portion, or like molecule retains the ability to enter and selectively kill transformed or neoplastic cells.

The synthetic peptides of the present invention may be synthesized by a number of known techniques. For example, the peptides may be prepared using the solid-phase technique initially described by Merrifield (1963) in *J. Am. Chem. Soc.* 85:2149-2154. Other peptide synthesis techniques may be found in M. Bodanszky et al. *Peptide Synthesis*, John Wiley and Sons, 2d Ed., (1976) and other references readily available to those skilled in the art. A summary of polypeptide synthesis techniques may be found in J. Sturart and J. S. Young, *Solid Phase Peptide Synthesis*, Pierce Chemical Company, Rockford, Ill., (1984). Peptides may also be synthesized by solution methods as described in *The Proteins*, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, *Protective Groups in Organic Chemistry*, Plenum Press, New York, N.Y. (1973). The peptides of the present invention may also be prepared by chemical or enzymatic cleavage from larger portions of the p53 protein or from the full length p53 protein. Likewise, leader sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

When applied to cells grown in culture, synthetic peptides are selectively lethal to malignant or transformed cells, resulting in dose dependent reduction in cell number. The effect is observable generally within two to three and at most 48 hours. A line of rat pancreatic acinar cells (BMRPA.430) grown in culture was transformed with K-ras. The normal cell line displays the architecture typical of pancreatic acinar cells; the transformed cells (TUC-3) lack the differentiated morphology of acinar cells, appearing as typical pancreatic cancer cells. When BMRPA.430 cells were treated with a synthetic peptide with the primary structure of SEQ ID NO:1 coupled to leader sequence SEQ ID NO:4, at a dosage of 50 μg/ml, the cells were not affected. However, when TUC-3 cells were treated with a peptide with the primary structure of SEQ ID NO:1 coupled to leader sequence SEQ ID NO:4, at a dosage of 100 μg/ml, they died within three to four days. Similar results were obtained when the same experiment was performed but SEQ ID NO:1 was substituted with either SEQ ID NO:2, or SEQ ID NO:3. Additionally, transformed and malignant cell death was observed in human breast carcinoma cell lines and Melanoma and HeLa cells treated with a synthetic peptide with the primary structure of SEQ ID NO:1 coupled to leader sequence SEQ ID NO:4, at a dosage of 100 μg/ml. In contrast, the same synthetic peptide at the same dosage had no effect on non-malignant and non-transformed human breast or fibroblast cell lines.

When the leader sequence set forth in SEQ ID NO:4 was positioned at the carboxy terminal end of PNC29, a control protein having the following amino acid sequence: MPFST-GKRIMLGE (SEQ ID NO: 25), there was no effect on malignant or normal cells.

Additionally, the peptide having the amino acid sequence as set forth in SEQ ID NO:3 fused at the carboxy terminal end to the leader peptide set forth in SEQ ID NO:4, has no effect on the ability of human stem cells to differentiate into hematopoietic cell lines in the presence of growth factors. This indicates that this peptide will not be injurious to bone marrow cells when administered as a chemotherapeutic agent. See Kanovsky et al., (Oct. 23, 2001) *Proc. Nat. Acad. Sci. USA* 98(22);12438-12443, the disclosure of which is incorporated by reference herein as if fully set forth.

When cultured cancer cells were treated with a peptide with the primary structure of SEQ ID NO:1 without a leader sequence attached, at a dosage of 100 µg/ml, the cells were unaffected. Similarly, when cultured cancer cells were treated with leader sequence SEQ ID NO:4, the presently preferred leader sequence, at the same dosage, the cell were also unaffected. These results indicate that the leader sequence of the synthetic peptide allows the synthetic peptide to cross the cellular membranes of treated cells and that the effect of the synthetic peptide is necessarily intracellular.

In order to determine whether the synthetic peptides acted by interfering with the binding of the p53 protein and the MDM-2 protein, the synthetic peptides were tested on transformed colorectal adenocarcinoma cells that had been rendered incapable of making the p53 protein by homozygous deletion. Surprisingly, the synthetic peptides selectively killed the transformed cells, but had no effect on the normal cells. These results indicate that the mechanism of action appears to be independent of the p53 protein binding to the MDM-2 protein, as the p53 peptide selectively kills transformed cells that do not produce the p53 protein at all. These results indicate that interference with binding of the p53 protein to the MDM-2 protein may not be the mechanism by which synthetic peptides cause selective death of malignant and transformed cells. Although the synthetic peptides disclosed herein, their derivatives, analogues, and peptidomimetic molecules are useful in the treatment of neoplastic disease such as cancer, the mechanism for action on transformed and malignant cells has not been discovered.

The peptides of the present invention are effective against neoplastic cells in vivo. For example, mice having been xenotransplanted with the pancreatic carcinoma cells BMRPA1. TUC-3 and having developed tumor size of about 3-6 mm, have the size of such tumors drastically reduced after administration of a subject synthetic peptide, e.g., a peptide having the amino acid sequence as set forth in SEQ ID NO:3 fused to a leader sequence at the carboxy terminal end.

Consistent with the observed properties of the peptides of the invention, the subject peptides may be used to selectively kill neoplastic or malignant cells, i.e., cancer cells in animals, preferentially humans. The synthetic peptides of the present invention are thus administered in an effective amount to kill neoplastic cells in a subject animal or human.

The synthetic peptides of the present invention may be administered preferably to a human patient as a pharmaceutical composition containing a therapeutically effective dose of at least one synthetic peptide according to the present invention together with a pharmaceutical acceptable carrier. The term "therapeutically effective amount" or "pharmaceutically effective amount" means the dose needed to produce in an individual, suppressed growth including selective killing of neoplastic or malignant cells, i.e., cancer cells.

Preferably, compositions containing one or more of the synthetic peptides of the present invention are administered intravenously for the purpose of selectively killing neoplastic cells, and therefore, treating neoplastic or malignant disease such as cancer. Examples of different cancers which may be effectively treated using one or more the peptides of the present invention include but are not limited to: breast cancer, prostate cancer, lung cancer, cervical cancer, colon cancer, melanoma, pancreatic cancer and all solid tissue tumors (epithelial cell tumors) and cancers of the blood including but not limited to lymphomas and leukemias.

Administration of the synthetic peptides of the present invention may be by oral, intravenous, intranasal, suppository, intraperitoneal, intramuscular, intradermal or subcutaneous administration or by infusion or implantation. When administered in such manner, the synthetic peptides of the present invention may be combined with other ingredients, such as carriers and/or adjuvants. There are no limitations on the nature of the other ingredients, except that they must be pharmaceutically acceptable, efficacious for their intended administration, cannot degrade the activity of the active ingredients of the compositions, and cannot impede importation of a subject peptide into a cell. The peptide compositions may also be impregnated into transdermal patches, or contained in subcutaneous inserts, preferably in a liquid or semi-liquid form which patch or insert time-releases therapeutically effective amounts of one or more of the subject synthetic peptides.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents. Examples of such agents include paraben, chlorbutanol, phenol, sorbic acid or thimerosal. Isotonic agents such as sugars or sodium chloride may also be incorporated into the subject compositions.

As used herein, a "pharmaceutically acceptable carrier" includes any and all solvents, dispersion media, coatings, antibacterial and antifungal agents, isotonic agents and the like. The use of such media and agents are well-known in the art.

Production of sterile injectable solutions containing the subject synthetic peptides is accomplished by incorporating one or more of the subject synthetic peptides described hereinabove in the required amount in the appropriate solvent with one or more of the various ingredients enumerated above, as required, followed by sterilization, preferably filter sterilization. In order to obtain a sterile powder, the above solutions are vacuum-dried or freeze-dried as necessary.

Inert diluents and/or assimilable edible carriers and the like may be part of the pharmaceutical compositions when the peptides are administered orally. The pharmaceutical compositions may be in hard or soft shell gelatin capsules, be compressed into tablets, or may be in an elixir, suspension, syrup or the like.

The subject synthetic peptides are thus compounded for convenient and effective administration in pharmaceutically effective amounts with a suitable pharmaceutically acceptable carrier in a therapeutically effective dosage. Examples of a pharmaceutically effective amount includes peptide concentrations in the range from about at least about 25 μg/ml to at least about 300 μg/ml.

A precise therapeutically effective amount of synthetic peptide to be used in the methods of the invention applied to humans cannot be stated due to variations in stage of neoplastic disease, tumor size and aggressiveness, the presence or extent of metastasis, etc. In addition, an individual's weight, gender, and overall health must be considered and will effect dosage. It can be generally stated, however, that the synthetic peptides of the present invention be administered in an amount of at least about 10 mg per dose, more preferably in an amount up to about 1000 mg per dose. Since the peptide compositions of the present invention will eventually be cleared from the bloodstream, re-administration of the pharmaceutical compositions is indicated and preferred.

The synthetic peptides of the present invention may be administered in a manner compatible with the dosage formulation and in such an amount as will be therapeutically effective. Systemic dosages depend on the age, weight, and condition of the patient and the administration route. An exemplary suitable dose for the administration to adult humans ranges from about 0.1 to about 20 mg per kilogram of body weight. Preferably, the dose is from about 0.1 to about 10 mg per kilogram of body weight.

In accordance with the present invention, there is also provided a method of treating neoplastic disease. The method comprises administering to a subject in need of such treatment, a therapeutically effective amount of a synthetic peptide hereinbefore described, including analogs and derivatives thereof. Thus for example, in one embodiment, an effective amount of a peptide comprising at least about six contiguous amino acids as set forth in SEQ ID NO:1 or an analog or derivative thereof fused on its carboxy terminal end to a leader sequence may be administered to a subject. In another embodiment, an effective amount of a peptide comprising at least from about eight (8) to at least about ten (10) contiguous amino acids as set forth in SEQ ID NO:1 or an analog or derivative thereof, fused on its carboxy terminal end to a leader sequence, may be administered to a subject. For example, an effective amount of a peptide having the amino acid sequence as set forth in SEQ ID NO:1 or an analog or derivative thereof, fused on its carboxy terminal end to a leader sequence may be administered to a subject. An effective amount of a peptide having the amino acid sequence as set forth in SEQ ID NO:2 or an analog or derivative thereof, fused on its carboxy terminal end to a leader sequence may also be administered to a subject. In still another embodiment, an effective amount of a peptide having the amino acid sequence set forth in SEQ ID NO:3 or an analog or derivative thereof, fused on its carboxy terminal end to a leader sequence may be administered to a subject. In accordance with a method of treatment, a mixture of synthetic peptides may be administered. Thus, for example, in addition to administering one of the peptides, or analogs or derivatives thereof hereinbefore described in an effective amount, mixtures of two or more peptides or analogs or derivatives hereinbefore described may be administered to a subject.

In another aspect of the present invention, there are provided expression vehicles comprising replication incompetent Adenovirus (AdV) and having a promoter sequence operably linked to a coding sequence for a subject peptide, e.g., nucleotide sequences encoding those peptides described above i.e., SEQ ID NO:1, SEQ ID NO:2, SEQ ID NO:3, or analogs or derivatives thereof as described fully above. As described above, more than one triplet (codon) can code for a particular amino acid residue. Table 2 shows the different combinations of codons which may be used to encode the amino acid sequences set forth in SEQ ID NO:1, SEQ ID NO:2, and SEQ ID NO:3. The amino acid sequence of SEQ ID NO:1 is shown in the top line of the table in bold. The amino acid sequences of both SEQ ID NO:2 and SEQ ID NO:3 can be found within this bolded portion. The bolded nucleotide sequence in Table 2 corresponds to the nucleotide sequence of PNC-28EG.

TABLE 2

| P | P | L | S | Q | E | T | F | S | D | L | W | K | L | L |
|---|---|---|---|---|---|---|---|---|---|---|---|---|---|---|
| CCU | CCU | TTA | TCT | CAA | GAA | ACT | TTC | TCC | GAT | TTA |  | AAG | TTA | TTA |
| CCC | CCC | TTG | TCC | CAG | GAG | ACC | TTT | TCT | GAC | CTC | TGG | AAA | CTC | CTC |
| CCA | CCA | CTT | TCA |  |  | ACA |  | TCA |  | CTT |  |  | CTT | CTT |
| CCG | CCG | CTC | TCG |  |  | ACG |  | TCG |  | TTG |  |  | TTG | TTG |
|  |  | CTA | AGT |  |  |  |  | AGT |  | CTA |  |  | CTA | CTA |
|  |  | CTG | AGC |  |  |  |  | AGC |  | CTG |  |  | CTG | CTG |

With respect to using nucleotide sequences encoding an analog or derivative of the amino acid sequences set forth in SEQ ID NOs:1, 2, or 3, one skilled in the art can refer to a table of the Genetic Code to select appropriate codons.

A number of different classes of Ad vectors exist, and may be used in the methods of the present invention. Such Ad vectors are described in the literature and are readily available. See e.g. Bramson et al., 1995, Hitt et al., 1996. For example, in accordance with the present invention, an Ad vector may be used wherein the E1 and/or E3 genes have been removed, allowing the introduction of up to about 6.5 kb of transgene under the control of a heterologous promoter. See Graham, F. L., J. Smiley et al. 1977. The defective E1 viruses may be propagated in an E1-complementing cell line, such as 293A cells, which cells provided the E1 gene in trans.

Alternatively, an Ad vector may be used which in addition to lacking the E1 and E3 genes, also lack the E2 genes. See e.g., Lusky, Christ et al., 1998, and O'Neal, Zhou et al., 1998.

In addition, helper-dependent (HD) or gutted vectors deleted of most or all Ad coding sequences may be used in accordance with the present invention. Such vectors have great potential as gene transfer vectors for gene therapy since long term expression of therapeutic genes have been observed in mice as well as monkeys. The production of these gutted vectors in tissue culture requires a complementing helper virus to provide the proteins required for growth and assembly of the gutted vector in trans. See Chen, Mack et al., 1997; Morral, N., R. J. Parks, et al. (1998); Morral, O'Neal et al., 1999. The disclosures of these papers and all references cited herein, are incorporated by reference as if fully set forth.

As discussed above, in the present application directed to viral therapy of neoplastic disease, e.g., cancer, where the goal of the therapy is clearance of the target tissue, a host anti-Ad immune response targeting the vector infected cells is considered desirable. Thus, a gutted Ad vector may not be as preferred as some of the earlier generation vectors which elicit a stronger immune response in the host.

An Ad vector may be based on a two-plasmid system, an entry plasmid and a destination vector made from E1 and E3 gene deleted adenoviral genome that contains a promoter operably linked to a nucleotide sequence encoding one of the peptides described above (SEQ ID Nos: 1-3) as well as analogs or derivatives thereof. The two-plasmid system is thoroughly described in Graham et al., 1977; Kozarksky and Wilson, 1993; and Krougliak and Graham, 1995). The E1 and E3 gene deletions prevent the virus from replicating in cells that do not express E1 and E3 proteins.

For example, the entry plasmid contains the gene encoding a subject peptide which plasmid is cloned into the AdV via a lambda recombination reaction. The replication incompetent vector may be propagated in 293A cells, which are bioengineered human embryonic kidney cells transformed by AdV genomic DNA (Wang et al., 2000). This cell line supplements the deficient genes required for viral replication.

The replication incompetent AdV vectors of the present invention can be constructed using standard recombinant DNA methods. Standard techniques for the construction of vectors are well-known to those of ordinary skill in the art and can be found in references such as Sambrook, Fritsch and Maniatis, 1989, or any of a number of laboratory manuals on recombinant DNA technology that are widely available. A variety of strategies are available for ligating fragments of DNA, the choice of which depends on the nature of the termini of the DNA fragments and can be readily determined by the skilled artisan. There are a number of different promoters which may be operably linked to the nucleotide sequences encoding a subject peptide. The promoter should function in the cells of a subject undergoing viral therapy with a subject AdV vector. There are a number of widely available promoters which may be used in the AdV vectors of the present invention. Examples of such promoters include, but are not limited to: CMV, SV40, RSV, LTR, beta-actin, EF-1 alpha, Gal-E1b, UbC, beta-Casein, EM-7, EF, TEF1, CMV-2 and Bsd. In a preferred embodiment, the promoter is CMV.

The recombinant vectors may then be subsequently rebuilt into intact viruses using standard methods such as that described in Stow, N. D. 1981, which is incorporated by reference herein as if fully set forth. Other references which describe rebuilding recombinant vectors into intact viruses include Crouzet J, L. Naudin et al., 1997, also incorporated by reference herein as if fully set forth.

Once a subject AdV vector is constructed, it may be used to treat patients suffering from different types of cancer. Therapy of neoplastic disease (cancer) may be accomplished by administering to a patient suffering from such disease a composition comprising the adenovirus vectors of the present invention. A human patient or nonhuman mammal suffering from a carcinoma may be treated by administering an effective antineoplastic dosage of a subject vector. The subject AdV vectors comprising a promoter operably linked to a nucleotide encoding a subject peptide are useful in treating a number of different cancers including but not limited to breast cancer, prostate cancer, lung cancer, cervical cancer, colon cancer, melanoma, pancreatic cancer, all solid tissue tumors (epithelial cell tumors) and cancers of the blood including but not limited to lymphomas and leukemias. In a preferred embodiment, the cancer to be treated is pancreatic cancer.

Suspensions of infectious adenovirus particles may be applied to neoplastic tissue by various routes, including intravenous, intraperitoneal, intramuscular, subdermal, and topical. Other routes include inhalation as a mist (e.g., in treating lung cancer) or direct application such as by swabbing a tumor site, e.g., cervical carcinoma, or during surgery if necessary. An adenovirus suspension may also be administered by infusion, e.g., into the peritoneal cavity for treating ovarian cancer. Other suitable routes include direct injection into a tumor mass, such as a breast tumor, via enema (colon cancer) or catheter in the case of bladder cancer.

The actual dosage may vary from patient to patient based on the age, weight, type and progression of cancer, location of tumor(s), presence of metastases, and overall condition of the patient. It can generally be said, however, that an adenovirus suspension containing about $10^3$ to about $10^{15}$ or more virion particles per ml may be administered. Re-administration of the AdV vector suspension may be performed as necessary.

The AdV vectors of the present invention may be admixed in a sterile composition containing a pharmacologically effective dosage of one or more subject AdV vectors. Generally speaking, the composition will comprise about $10^3$ to about $10^{15}$ or more AdV particles in an aqueous suspension. The sterile composition is usually an aqueous solution such as e.g., water, buffered water, 0.4% saline, 0.3% glycine and the like. Such compositions may contain pharmaceutically acceptable auxiliary substances e.g., to mimic physiological conditions such as pH adjusting and buffering agents, toxicity adjusting agents and the like, e.g., sodium acetate, sodium chloride, potassium chloride, calcium chloride, sodium lactate, etc. The compositions may also comprise excipients that enhance infection of cells by the subject AdV vectors.

The following examples further illustrate the invention and are not meant to limit the scope thereof.

EXAMPLE I

The following experiment was performed to compare effectiveness of subject peptides having the leader sequence attached to the amino terminal end. As described supra, peptides synthesized with a leader sequence on the carboxyl terminal promoted α-helix formation in the peptide, which is the active conformation of the p53 part of this peptide when bound to MDM-2. As described supra, subject peptides having the amino acid sequences as set forth in SEQ ID NOs:1, 2, and 3 are strongly toxic to a wide variety of human cancer cells, including those that are homozygously p53 gene-deleted. An α-helix probability profile for each peptide having the sequences set forth in SEQ ID NOs:1-3 was performed using two different methods, one using helix probabilities from the protein database (Karplus, K. et al., (1998) Bioinformatics 14:846-856), and the other using the Ising model based on helix nucleation (σ) and growth (s), equilibrium constants determined experimentally from block copolymers for each of the twenty naturally occurring L amino acids, modified by inclusion of the effects of charges on these parameters as described in Vasquez, M., et al. (1987) Biopolymers 26:351-372 and Vasquez, M., et al., (1987) Biopolymers 26:373-393. Probability profiles indicated that if the leader sequence is on the amino terminal end, even though the peptide still transverses the cell membrane, the α-helical content is much lower.

The peptide having the sequence set forth in SEQ ID NO:3 was synthesized by solid phase synthesis with the leader sequence attached to the amino terminal end. This peptide is labeled PNC28' in Table 2 below. The PNC28' peptide was incubated with transformed pancreatic cancer (TUC-3) cells at three different concentrations, i.e., 25, 50 and 100 µg/ml. After two weeks of incubation, at the highest dose of peptide, there was no cell death, and approximately half of the cells were seen to form acini and exhibited the untransformed morphological phenotype. The same phenomena were observed at 50 µg/ml, and at 25 µg/ml significantly fewer cells were seen to revert. In contrast, when the leader sequence was attached to the carboxyl terminal end of the peptide (PNC28 in Table 2), at dosages of 50 and 100 µg/ml. 100% cell death occurred in about 4 days.

These results show that the leader sequence is preferentially added to the carboxyl terminal end of the MDM-2 portion of the p53 peptide to enable the peptide to cross the cell membrane and specifically kill malignant cells. In Table 3, the leader sequence is KKWKMRRNQFWVKVQRG (SEQ ID NO:4).

TABLE 3

| NAME | p53 seq. | PEPTIDE | EFFECT |
|---|---|---|---|
| 1. PNC 21 | 12-20 | (PPLSQETFS) (SEQ ID NO: 2) - Leader | Cytotoxic |
| 2. PNC 27 | 12-26 | (PPLSQETFSDLWKLL) (SEQ ID NO: 1) - Leader | Cytotoxic |
| 3. PNC 28 | 17-26 | (ETFSDLWKLL) (SEQ ID NO: 3) - Leader | Cytotoxic |
| 4. PNC 28' | 17-26 | Leader (ETFSDLWKLL) (SEQ ID NO: 3) | No cell death and reversion |

These results indicate the uniqueness of the subject peptides. i.e., the leader or cluster of positively charged residues must be placed at the carboxy terminal end of any effector peptide for cancer cell toxicity.

EXAMPLE II

Nu/Nu mice (Harlan Laboratories, Indianapolis, Ind., n=10) and weighing 20-22 g, were xenotransplanted subcutaneously (s.c.) with live pancreatic carcinoma cells BMRPA1.TUC-3 ($1 \times 10^6$ cells/mouse) in the left hind region. Tumors were allowed to develop and grow and during daily examinations it was observed that all mice developed tumors with very similar growth rates.

After 12 days the tumors had reached sizes of 3 to 6 mm diameter and the mice were separated into two groups of 5 mice each. Each group was implanted s.c. with Alzet® osmotic pumps to deliver in a constant rate and over a defined period of 14 days a total volume of 0.095 ml volume of normal saline containing the respective peptide at a concentration of 20 mg/mouse. One group of mice received PNC-28 (the peptide having the amino acid set forth in SEQ ID NO:3) fused at its carboxy terminal end to the penetratin leader sequence (SEQ ID NO:4) and the other group of mice received PNC-29, a control peptide of similar size, having the following amino acid sequence: MPFSTGKRIMLGE (SEQ ID NO: 25). The pumps were filled according to the manufacturers guidelines and under sterile conditions The pumps were implanted s.c. on the left flank of the anaesthetized mice by creating a pocket underneath the mouse skin into which the tiny pumps were inserted. Each pocket was closed with a simple suture. From their inside chamber the pumps delivered continuously 0.25 µl/hr into each mouse. The mice were observed until they had recovered from the surgery when they were returned to the isolation ward of the animal facility. Since the animals were Nu/Nu mice and, thus, immunocompromised they are highly susceptible when exposed to pathogens. Surgery and all preceding and post-surgical treatments were therefore performed in a sterile hood environment.

As shown clearly in FIG. 1, PNC-28 within a 48 to 72 hr period of delivery into the mouse effectively arrests tumor growth. In contrast, the control peptide PNC-29 had no effect on normal or tumor cells. In PNC29-treated mice, tumors kept growing at a continuous rate resulting in tumors of 10 to 16 mm diameter over the 2-week treatment and follow-up period when the pumps cease to release any more peptide solution. Statistical analyses of the measurement of tumor size in both groups of mice has produced a significance between them of $p<0.001$.

EXAMPLE III

Using the same methodology of Example II, pumps were started at the same time as live pancreatic carcinoma cells BMRPA1.TUC-3 ($1 \times 10^6$ cells/mouse) were xenotransplanted into mice (n=10). Five mice were administered PNC28 and 5 mice were not treated at all (sham treated). Results are tabulated below.

TABLE 4

| Treatment | 7 Days | 14 Days | 21 Days |
|---|---|---|---|
| | | Tumor Size | |
| Sham treated | 4.8 ± 1.8 | 11.7 ± 2.3 | 14.8 ± 3.6 |
| PNC-28 treated | 3 ± .6 | 3.1 ± .9 | 4.4 ± .8 |

EXAMPLE IV

Using the same methodology as described in Example II, live pancreatic carcinoma cells BMRPA1. TUC-3 ($1 \times 10^6$ cells/mouse) were transplanted to the peritoneal cavity of five mice. Pumps were placed in the right shoulder region at the same time of tumor cell transplantation. In all five mice, there were no visible tumors after three weeks.

EXAMPLE V

Materials and Methods in AdV Vector Construction

Cells and Cell Culture: 293A cells obtained from Invitrogen (Carlsbad, Calif.) were thawed from cryovials and grown in 75 cm² tissue culture flasks (TCF, Corning) in a medium composed of DMEM, 2 mM L-glutamine, 10% Fetal Bovine Serum (FBS, Atlanta Biologicals, Norcross, Ga.) and 1% Penicillin-Streptomycin (cDMEM). Cells were grown at 37° C. in an incubator supplied with a $CO_2$-95% air mixture. The medium was changed every 2 days. When cells were 90-95% confluent they were washed with 1×PBS, released with 1× Trypsin and passaged into fresh TCF.

BMRPA1. TUC3 cells (live pancreatic carcinoma cells) were produced by transfection of normal rat pancreatic acinar cells (BMRPA1) with a plasmid containing human k-ras gene with an oncogenic mutation in codon 12 (Gly 12→Val 12) and a neomycin resistance gene. Uncontrolled cell proliferation in vitro, loss of contact inhibition, growth in low nutrient medium and tumor formation in vivo are characteristics of this transformed pancreatic cell line. (Bradu, 2000; see also copending provisional patent application Ser. No. 60/440, 699, filed Jan. 17, 2003, which application is incorporated by reference herein as if fully set forth). BMRPA1. TUC3 cells were grown in semisynthetic RPMI medium containing trace elements, growth factors and 10% FBS (cRPMD (Bradu, 2000). Medium was changed every 2 d and cells were passaged at 90-95% confluency.

Synthesis of PNC-28EG: Two single stranded DNA fragments containing the peptide sequence, an initiation codon (ATG), a stop codon (TAG), Not I and Kpn I restriction sites (New England BioLabs Inc, Beverly, Mass.) and an additional 4 base pairs, which are necessary for proper restriction enzyme binding were synthesized for this study by Invitrogen, Carlsbad, Calif. The two single strands were annealed at 95° C. for 5 min and were amplified through PCR in a reaction volume of 25 µl using the following primers: GAGTGCG-GCCGCTTCTAGAGG (PNC-28EG-Rev)(SEQ.ID. No. 26), ATCCGGTACCAAATGGAGACC (PNC-28EG-Frw)(SEQ.ID. No. 27) and Taq polymerase. In order to prevent the likelihood of mispriming, PNC-28EG-Frw and Rev were used at a concentration of 10 pmoles. Subsequently 5 µl of PCR product were analyzed on a 2% agarose gel along with a 100 bp marker (Invitrogen) to verify the gene's length of 62 bp.

Polymerase Chain Reaction: Polymerase-chain-reaction (PCR) is a method that serves to amplify a distinct DNA fragment in vitro. For this purpose, double stranded DNA is first denatured and then annealed with two complementary oligonucleotides (primers) that flank the DNA fragment to be replicated. The DNA fragment between the two primers was synthesized using Taq Polymerase (Qiagen, Valencia, Calif.). Through repetition of these three steps the original segment is ideally amplified $2^x$-times, whereby x stands for the number of cycles (Saiki et al., 1985). Finally all incomplete strand syntheses were completed by an additional longer extension time. Unless stated otherwise, the PCR conditions were as follows: 5 min 95° C. (Denaturing), followed by 30 cycles of 1 min 95° C. (Denaturing), 1 min 50° C. (Annealing), 1 min 72° C. (Extension) followed by a final extension time of 10 min at 72° C.

Unless stated otherwise all PCR products were analyzed in a 2% agarose gel made with 2 g of agarose (Bio-Rad Laboratories, Hercules, Calif.) per 100 ml of 1×TBE (Tris, Boric Acid, EDTA) containing 7.5 µl of Ethidium Bromide (10 mg/ml) to stain the DNA bands. DNA products were separated on the gel at 70 volts (V) and analyzed via ultra violet illumination.

Cloning PNC-28EG in pCR 2.1 Topo and transforming TOP 10 competent *E. Coli*: In order to sequence PNC-28EG, the PCR product was cloned into pCR 2.1 Topo vector (Invitrogen) following Invitrogen's TOPO cloning and transformation protocol. pCR 2.1 Topo/PNC-28EG vector (2 µl) was added to TOP 10 chemical competent *E. coli* (Invitrogen) and incubated on ice for 30 min, heat shocked in a water bath at 42° C., incubated in 250 µl of SOC medium (Invitrogen) and shook at 200 rpm for 1 hr at 37° C. 100 µl of this mixture were plated on selective ampicillin (50 µg/µl) agar plates. Bacteria were allowed to propagate overnight and colonies analyzed via PCR for the presence of the correctly sized gene.

Analysis of Bacteria Colonies for pCR 2.1 Topo/PNC-28EG: Several reaction mixtures were prepared with each containing 1 µl PNC-28EG-Rev (10 pmol), 1 µl PNC28EG-Frw (10 pmol), 0.5 µl dNTP's (Qiagen), 0.5 µl Taq Polymerase, 2.5 µl 10× Buffer (Qiagen) and 19.5 µl sterile water was prepared. Selected colonies were picked with an inoculation loop and transferred into pre-labeled 0.5 ml polypropylene tubes (USA Scientific, Ocala, Fla.) containing the reaction mixture and a PCR was performed. Loading buffer (5 µl), and 5× Ficoll, were added to 8 µl of PCR product, and the PCR products were analyzed on a 2% agarose gel.

Colonies containing the recombinant plasmid were grown overnight at 37° C. in Lurea Bertani (LB) broth (LB broth with 50 µg/µl of Ampicillin). Bacteria were harvested and pCR 2.1 Topo/PNC-28EG was isolated using Qiagen's Miniprep plasmid isolation kit. The concentration of the isolated plasmids was measured at $OD_{260nm/280nm}$ prior to sequencing.

Construction of Entry vector (pENTRII/PNC-28EG): The entry vector was constructed by cloning PNC-28EG into pENTR11. PNC-28EG was purified from pCR 2.1 Topo and ligated to the exposed termini of pENTR11 according to the manufacturer's directions (Invitrogen). For the ligation pCR 2.1 Topo/PNC-28EG and pENTR-11 were digested with Kpn1, Not1 (New England BioLabs Inc, Beverly, Mass.) the DNA fragments separated on an agarose gel and purified by gel extraction.

Kpn I digestion: 60 µg of the pCR 2.1 Topo/PNC-28 were digested at 37° C. for 1 hr with 60 units of Kpn I in a 50 µl reaction volume containing 30 µl of pCR 2.1 Topo/PNC-28 (2 µg/µl), 6 µl Kpn1 (10 units/µl), 5 µl 10× Buffer (supplied with enzyme) and 9 µl of sterile water. Digestion was followed by phenol chloroform extraction and ethanol precipitation to remove proteins and enzymes that could interfere with further digestion by Not1. 25 µl of 1:1 phenol chloroform were added to the digested samples. Samples were vortexed for 15 sec and centrifuged at 13,000 rpm for 3 min. Three layers were identifiable in the sample after centrifugation: the top layer containing the plasmid was carefully transferred into a new tube without disturbing the middle layer or interphase. Plasmids were then precipitated by adding 100 µl of 100% ethanol and 5 µl of 3M Na-acetate and then placed at –80° C. One hour later, the tubes were removed from –80° C. and centrifuged at 13,000 rpm for 20 min to pellet the plasmid. Supernatant was removed without disturbing the pellet. Pre-chilled 70% Ethanol (150 µl) was added and the tubes were subjected to another 5 min centrifugation. All traces of Ethanol were removed from the tubes and the pellet was left to air dry for 10 min.

Not1 digestion: The pellet was re-eluted with 38.5 µl of sterile water and digested with Not1 under the same conditions for the Kpn I digestion described above, i.e. 60 units of Not1 (6 µl), 5 µl of 10× Buffer (supplied with Not1 enzyme), 0.5 µl of 100×BSA and 38.5 µl of sterile water, at 37° C. for 1 hr.

pENTR11 (20 µg) was processed by Kpn I and Not I restriction enzyme digestion in parallel with the pCR 2.1 Topo/PNC-28EG vector in the same manner as described for pCR 2.1 Topo/PNC-28EG Entry vector.

Gel Extraction: Ficoll (5×, 20 µl) was added to the 50 µl reaction volume and the entire mixture was separated on a 1% agarose gel at 70V for 5 min. The gel was analyzed under UV lighting where the appropriately sized band containing PNC-28EG was excised. PNC-28EG was purified from the agarose slab using Qiagen's Gel Extraction Kit. PNC-28EG was then ligated to the linearized pENTR11 by T4 DNA ligase (New England Bio Labs Inc, Beverly, Mass.) to construct the pENTR11/PNC-28EG Entry vector.

Ligation: Both samples were quantitated at $OD_{260nm/280nm}$ and the final concentration of both samples required for ligation determined. A ligation reaction containing 8.5 µl PNC-28 EG, 8.5 µl of pENTR11, 1 µl of T4-DNA ligase, 2 µl of 10× buffer (supplied with ligase) was performed. The reaction mixture was incubated at 16° C. for 4 hr. 2 µl of the ligation reaction were transformed into *E. coli*. The transformed *E. coli* mixture (100 µl) was spread on selective Kanamycin (50 µg/ml) agar plates (50 µg/µl). Colonies that grew on the plates were subjected to PCR amplification using PNC-28EG priming oglionucleotides (PNC-28EG Frw and Rev) as specific primers. The product was analyzed on a 2% agarose gel to determine proper ligation of PNC-28EG to pENTR11. A PNC-28EG positive colony was selected and grown over night in 25 ml of liquid culture containing 50 µg/µl of Kanamycin. The pENTR11/PNC-28 vector was isolated from the Bacteria using Qiagen's miniprep isolation kit.

Construction of AdV containing PNC-28 (pAd/CMV/V5/PNC-28EG): The completed pENTR-11/PNC-28EG (202.5 ng) was cloned into 150 ng of the pAD/CMV/V5-DEST vector during an incubation at 25° C. for 2 hrs following Invitrogen's lambda recombination (LR) protocol. Reaction mixture (1 µl) was used to transform E. coli, which were then plated on selective Ampicillin agar plates. After overnight growth colonies were picked at random and subjected to PCR amplification using the PNC-28EG oligonucleotides as specific primers. PNC-28EG positive colonies were cultured in selective ampicillin LB broth, and their vectors isolated for DNA sequencing. From the vector that contained the correct DNA sequence of PNC-28EG, 4 µg were digested with Pac I restriction enzyme (New England Bio Labs Inc, Beverly, Mass.) and transfected into 293A cells to propagate the newly constructed virus (pAd/CMV/V5/PNC-28EG).

Transfection of 293A cells to propagate the pAd/CMV/V5-GW/LacZ Virus: 293A cells were seeded at $5 \times 10^5$ cells per well in a 6 well dish containing 2 ml of cDMEM on the day before transfection. On the day of transfection cDMEM was replaced with 1.5 ml of Opti-MEM (Invitrogen) containing 10% FBS. 1 µg of pac I digested pAD/CMV/V5-GW/LacZ vector was diluted in 250 µl of Opti-MEM and 3 µl of Lipofectamine 2000 were diluted in 250 µl of Opti-MEM. Solutions were incubated at room temperature (RT) for 5 min, combined and incubated for another 20 min at RT. The combined solution was added to the wells of the 6-well dishes and the cells incubated at 37° C. and fed every 2-3 days. Cells were allowed to grow until cytolysis was apparent (up to 14 days). After 80-90% of the cells were lysed, virus containing supernatant was harvested following a method of freezing (−80° C.) and thawing (37° C.) the cell suspension. After 3 cycles of freezing and thawing, cell fragments were pelleted by centrifugation at 3000 rpm for 15 min, the supernatant recovered and aliquoted into 1 ml cryovials and stored at −80° C. for future use.

Transduction of BMRAP1. TUC-3 with pAD/CMV/V5-GW/LacZ Virus: Cells are said to be transduced rather than transfected when the virus is unable to replicate in the cell line. On the day before transduction BMRAP1. TUC-3 cells were seeded in a 6 well plate at a density of $1 \times 10^5$ cells per well. On the day of transduction pAd/CMV/V5-GW/LacZ virus was diluted in ten fold dilutions from $10^{-9}$ to $10^{-4}$ into cRPMI, in a final volume of 1 ml. Spent culture medium was removed and the 1 ml dilutions of the pAd/CMV/V5-GW/LacZ virus were added to their respective wells. The next day the culture medium containing the virus was removed from each well and 2 ml of pre-warmed (65° C.) agarose overlay consisting of plaquing medium (cRPMI with 3% FBS) and 4% agarose were added to each well. The plate was returned to a 37° C. humidified $CO_2$ incubator. Three days after the addition of the first overlay, 1 ml of additional overlay was added to each well. 293A cells were transfected in the same manner with the pAd/CMV/V5-GW/LacZ virus in order to provide a control. BMRAP1. TUC-3 and 293A cells were monitored over a 14 day period for signs of cytolysis.

Transfection of BMRPA1. TUC3 Cells with pAd/CMV/V5/PNC-28EG Vector: On the day of transfection BMRAP1. TUC3 cells were released and seeded into a 6-well plate at a density of $1 \times 10^5$ cells in antibiotic-free cRPMI medium containing 10% FBS and allowed to adhere for 4 hrs. pAd/CMV/V5/PNC-28EG vector (4.0 µg) was diluted in 250 µl of Opti-MEM and 4 µg and 10 µl of Lipofectamine 2000 was diluted in 250 µl of Opti-MEM. The solutions were incubated at RT for 5 min, combined and further incubated for 20 min at RT. Then the mixture was added to the cells. For controls, a set of BMRAP1. TUC3 cells were transfected with pAD/CMV/V5-GW/LacZ vector and a third set of cells received only 10 µl of Lipofectamine 2000. The plates were returned into a 37° C. humidified $CO_2$ incubator. Twenty-four and 48 hrs later the supernatants in each set of wells were collected (2 ml), centrifuged, and the pelleted non-adherent cells counted. Each time the wells were replenished with 2 ml of fresh medium. Seventy-two hours post transfection, after the supernatant from each well was collected and non-adherent cells counted, the adherent-cells were released in 0.5 ml of 1× trypsin, counted using a hemocytometer and trypan blue exclusion (Michl et al., 1976). Photography was done on an inverted size Zeiss microscope with 400 ASA Fuji film.

EXAMPLE VI

Results

The construction of the adenoviral vector is based on conservative site-specific recombination. Bacteriophage lambda, a bacterial virus, was the first micro entity to be understood that exhibited conservative site-specific recombination. When the virus enters its host cell an enzyme called lambda integrase is synthesized. This enzyme mediates the covalent joining of the viral DNA into the bacterial chromosome allowing the viral DNA to be replicated as and integral part of the host's DNA (Alberts et al., 2001). Recombination is based on related but different DNA recognition sites found on the bacteriophage and the bacterial chromosome. Bacteriophage integrase binds to the DNA sequence found on the bacteriophage and forms a DNA-protein complex. This complex is able to bind to the attachment DNA sequence found on the bacterial chromosome. Integrase is then able to catalyze a reaction that cuts and reseals the DNA resulting in a site specific strand exchange.

The same mechanism that drives bacteriophage-host integration is present in the design of the adenoviral vector pAd/CMV/V5/PNC-28EG. The gene encoding PNC-28 (PNC-28EG) was cloned into an entry plasmid that lacks promoters necessary for expression of PNC-28EG and thus is said to be transcriptionally silent. The entry plasmid contains specific recombination sites, which flank the transgene and correspond with recombination sites in the adenoviral destination vector, pAd/CMV/V5-DEST. pAd/CMV/V5-DEST vector contains the necessary promoters that will drive the transcription and translation of PNC-28EG. Through a recombinant reaction, PNC-28EG is subcloned into the pAd/CMV/V5-DEST vector to create the adenoviral vector pAd/CMV/V5/PNC-28EG. pAd/CMV/V5/PNC-28EG contains Human Adenovirus type 5 sequence encoding genes and elements required for proper viral packaging and adenovirus production. However it is deficient in E1 and E3 sequences rendering it replication incompetent in cell lines that do not supply these genes.

Before the newly constructed pAd/CMV/V5/PNC-28EG vector can be tested as an anti-cancer agent in pancreatic cancer cells, it is important to determine the replicable nature of the virus. As mentioned above, pAD/CMV/V5/PNC-28EG lacks the E1 and E3 sequences found in the adenoviral genome and can only replicate in cell lines such as 293A that were bioengineered to express these deficient genes (Wang et al., 2000). The complete genome of every mammalian cell line is still unknown and, therefore, it was uncertain whether the pancreatic carcinoma cell line, BMRPA1. TUC-3, expresses these genes and in turn will support the replication of this type of Ad virus possibly resulting in cell death. PNC-28 induces cytolysis in pancreatic carcinoma; however, the mechanisms that drive viral replication in competent cells also induce cell death. For the development of pAd/CMV/V5/PNC-28EG into a therapeutic tool, it was important to ensure that cell death in Pancreatic carcinoma cells was due to the transcription and translation of the PNC-28 gene and not due to virus replication.

Figure 2:
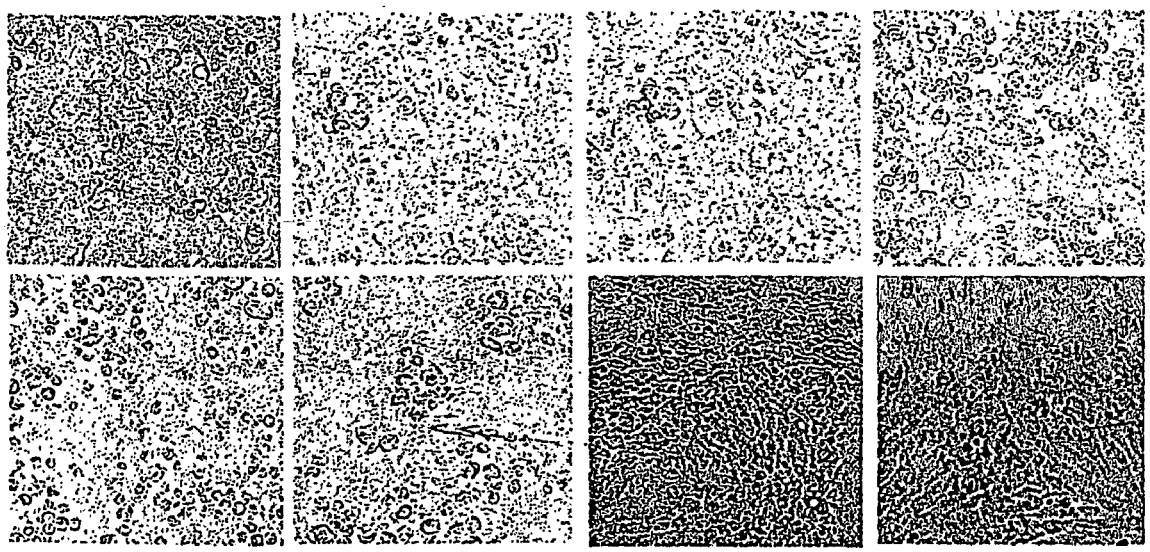
FIGS. 2A through 2H are photomicrographs showing the effect of pAD/CMV/V5-GW/LacZ virus on 293A and BMRPA1.TUC3 cells.

In order to determine the cause of cytolysis in pAd/CMV/V5/PNC-28EG transfected cells, a control Adenoviral vector that lacked PNC-28EG was needed—pAD/CMV/V5-GW/LacZ. pAd/CMV/V5-GW/LacZ is identical to the constructed pAd/CMV/V5/PNC-28EG vector, except it contained the LacZ gene instead of PNC-28EG. The control vector provided two benefits: It lacked PNC-28EG and therefore served as a control and galactosidase expression can be easily detected. A crude viral stock was obtained by transfecting 293A cells with pAD/CMV/V5-GW/LacZ and a lipid based transfection reagent, lipofectamine 2000. The virus was harvested when 80-90% of the adherent cells were lysed. This initial stock contained a viral titer of $1 \times 10^7$ to $1 \times 10^8$ plaque forming units (pfu). The crude viral stock was used to transfect 293A cells again to produce a higher titer. A titer of $1 \times 10^8$ to $1 \times 10^9$ pfu was obtained and such a high titer is desired. Six ten-fold dilutions were made to the pAd/CMV/V5-GW/LacZ virus stock ranging from $10^{-9}$ to $10^{-4}$. These dilutions were added to the wells of a 6-well plate containing 293A and a second 6-well plate containing BMRAP1. TUC3 cells, respectively. Since the virus replicated in 293A cells, lysis of 293A cells served as a control for verifying that the virus was working properly. The next day an agarose overlay was placed over the cells and they were monitored for the formation of plaques over the course of two weeks, with the addition of adding a second agarose overlay, 4 days following the first. As FIG. 2 shows, clear morphological changes were noted in 293A, but not in BMRPA1. TUC3 cells.

FIGS. 2A-2H show the effect of the pAD/CMV/V5-GW/LacZ virtus on 293A and BMRPA1. TUC3 cells. FIGS. 2A-2F are photomicrographs of dilutions of 293A cells ($10^{-9}$ to $10^{-4}$ of pAD/CMV/V5-GW/LacZ virus). After 14 days, the morphology of the 293A cells has changed. At the $10^{-9}$ dilution 90% of the cells are still confluent but cytolysis is not visible. With increasing concentration of pAD/CMV/V5-GW/LacZ virus, large areas of rounding and dying cells are visible. Only a few regions of low confluency are detectable at concentrations of pAd/CMV/V5-GW/LacZ greater than $10^{-5}$.

FIGS. 2G and 2H are photomicrographs of dilutions of BMRPA1. TUC3 cells to which $10^{-9}$ to $10^{-4}$ of pAD/CMV/V5-GW/LacZ virus were added. No visible signs of cell lysis are detectable in the BMRPA1. TUC3 cultures at any of the pAd/CMV/V5-GW/LacZ dilutions ($10^{-8}$-$10^{-5}$ not shown) and cells are confluent at the $10^{-4}$ dilution (FIG. 2H) as they are at the lowest concentration, $10^{-9}$ dilution, (FIG. 2G).

The BMRPA1. TUC-3 cells showed no sign of cytolysis or cell death. This indicates that BMRAP1. TUC3 cells do not supplement the deleted E1 and E3 genes and, as a result, the virus is replication incompetent. If the virus would have caused cytolysis in BMRPA1. TUC3 cultures then it would not be considered a suitable candidate vehicle for introducing the cytotoxic PNC-28 gene into the target cells.

Construction of AD/CMV/V5/PNC-28:

Synthesis of PNC-28EG was the first step in Ad vector construction. Two oglionucleotides, which corresponded with the amino acid sequence of PNC-28 (ETFSDLWKLL) as published by Kanovsky et al., (2001) were synthesized. In addition to encoding the PNC-28 peptide, the oglionucleotide sequence also contained an initiation codon, a stop codon, Kpn I and Not I cleavage sites and 4 additional bases on each end, which stabilized the DNA fragment and were necessary for proper enzyme binding to the restriction sites. Kpn1 and Not1 restriction sites were chosen because they were present in the multiple cloning site (MCS) of the pENTR-11 vector. The cleavage of the Kpn1 and Not1 restriction sites on pENTR-11 exposed protruding termini and allowed the ligation of PNC-28EG with a total sequence of 62 bps (FIG. 3) into the pENTR11 vector.

According to the manufacturer's information (Invitrogen) during the synthesis of oligonucleotides the probability of incorrect synthesis is 0.99 per nucleotide. Thus, the probability of this oligonucleotide being synthesized correctly is $0.99^{62}$ and the probability of two correct strands annealing to form the desired dimer is $(0.99^{62})^2$. Therefore, the annealed PNC-28EG was used as a template for PCR amplification to amplify the desired annealing product exponentially and, in doing so, increasing the probability of an excess of this DNA being cloned into the respective vector. Deletions or point-mutations would very likely alter or shift the reading frame for DNA translation during protein synthesis and result in ineffectual, shortened or no protein being transcribed.

Figure 4:
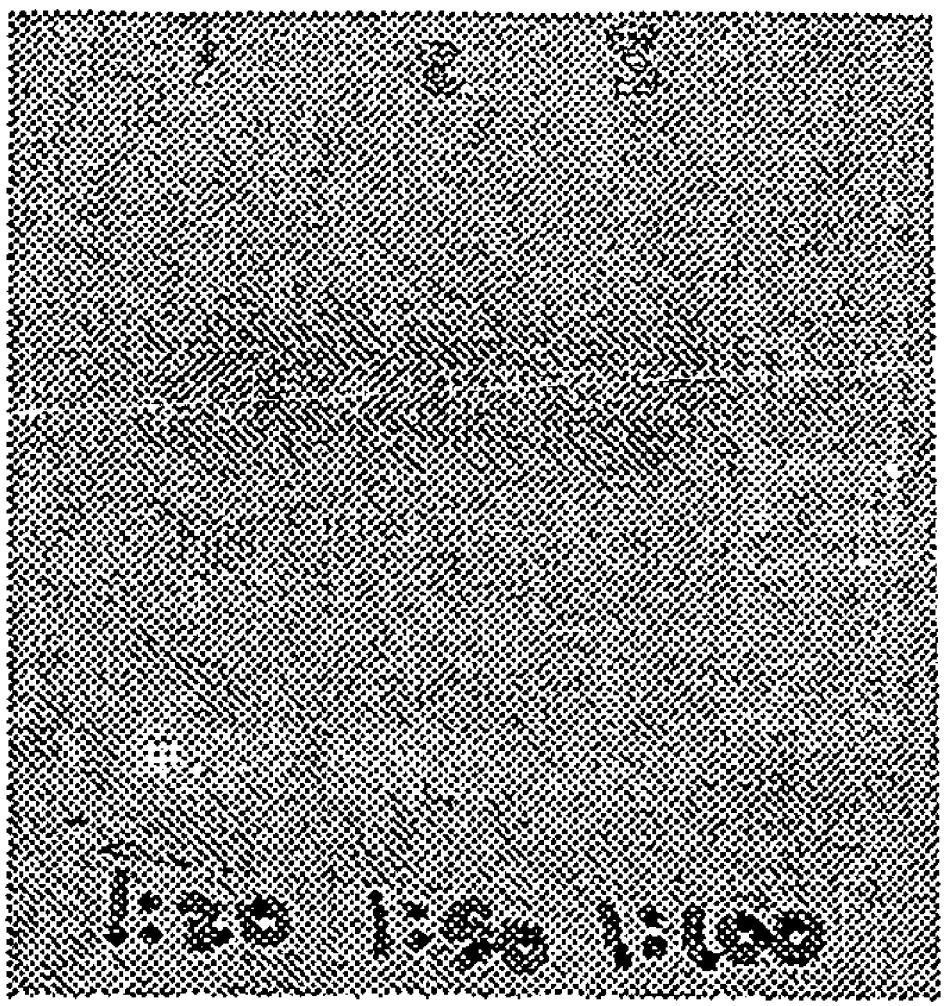
FIG. 4 is a gel photograph showing the PNC-28EG PCR product. Lane 4 contains a 100 bp marker.

Two priming oglionucleotides were synthesized. One was complementary to PNC-28EG in the 5'-3' direction, GAGTGCGGCCGCTTCTAGAGG (PNC-28EG-Frw)(SEQ.ID. No. 27) and the other one in the 3'-5' direction, ATCCGGTACCAAATGGAGACC (PNC-28EG-Rev)(SEQ.ID. No. 26). Gel electrophoresis was then used to identify the molecular size of the amplified PNC-28EG. A size of 62 bps indicates proper annealing and amplification of PNC-28EG. FIG. 4 shows the PCR product (Lanes 1, 2, 3) as determined by comparison to a 100 bp marker (lane 4). Three different dilutions of the PCR product (1:20, 1:50, and 1:100). They were separated on lanes 1, 2, and 3 respectively.

The proper molecular size of the 62 bp bands indicates that no deletions were made in the sequence. Further analysis by DNA sequencing (Sambrook et al, 1989) of the excised band showed that no alterations were present. This step was vital because DNA Taq polymerase used in the reaction misincorporates nucleotides at a rate of $2 \times 10^{-4}$ nucleotides per cycle.

Figure 5:
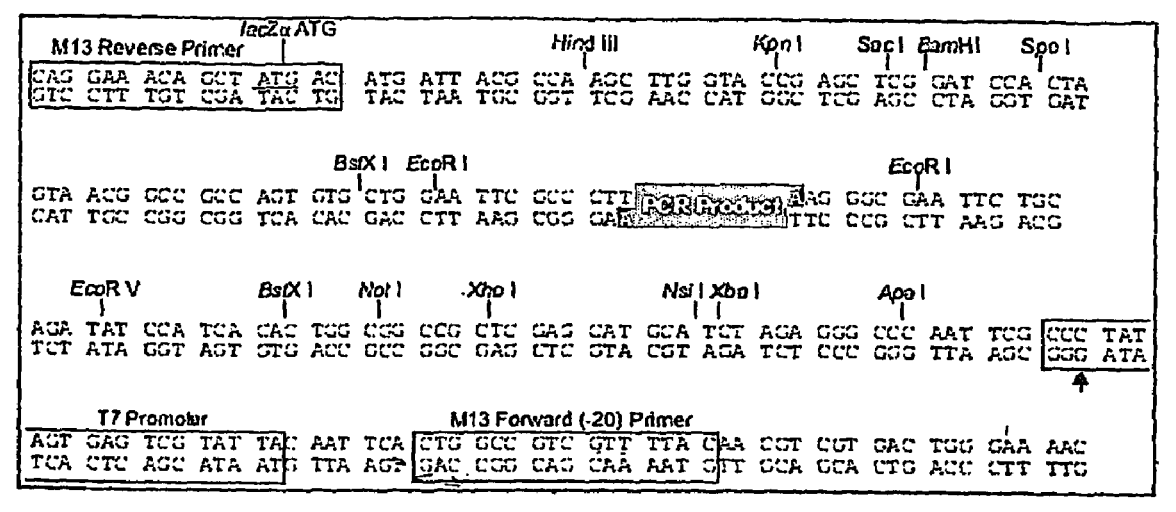

The strategy used for sequencing PNC-28EG was cloning the gene into a plasmid that contained universal priming sites, transforming this recombinant plasmid into competent *E. Coli*, purifying the recombinant plasmid from the selectively grown colonies that contained the plasmid and sending the plasmid DNA for sequencing. PNC-28EG was cloned into the pCR 2.1 Topo vector. This plasmid was chosen because it provided fast and efficient insertion of the PCR product into the vector through the use of Topoisomerase I. Topoisomerase I ligates deoxyadenosine (A) overhangs produced by Taq polymerase on the 3' end of PNC-28EG to the 3' overhangs of deoxythymidine (T) present on the linearized vector. The pCR 2.1 Topo vector contained ampicillin, kanamycin selective markers and a lacZ gene, which allowed for selection of bacterial colonies that harbored the recombinant plasmid. The cloning site for pCR 2.1 Topo is shown in FIG. 5. As shown in FIG. 5, the cloned gene lies within the sequence range of the universal M13 primers which are used as sequencing primers. The vector contains the ampicillin and kanamycin resistance genes and the lacZ gene.

The pCR 2.1 TOPO/PNC-28EG recombinant plasmid was then transformed into competent *E. coli* by adding the ligated plasmid mixture to thawed TOP10 competent bacteria cells and briefly heating the cells. This brief change in temperature allowed the bacterial cell to take up the plasmid. The transformed bacterial cells were grown on selective ampicillin plates that contained x-gal. The LacZ gene present in pCR 2.1 TOPO/PNC-28EG was used to screen for positive colonies, i.e. colonies that contain the plasmid. LacZ encodes for β-galactosidase, which metabolizes β-galactoside X-gal and this produces a blue color (Invitrogen). The cloning of PNC-28EG into the pCR 2.1 Topo plasmid prevents the expression of LacZ. Therefore pCR 2.1 TOPO/PNC-28EG positive colonies will not exhibit a blue color. Ampicillin added to the culture plates prevents the growth of pCR 2.1 TOPO/PNC-28EG negative bacteria, because they lack the ampicillin resistance gene found in the plasmid. Finally, PCR is used to screen among the white colonies for false positives, or colonies that do not contain PNC-28EG. The bacterial colonies served as templates for the priming oglionucleotides PNC-28EG-Frw and PNC-28-Rev, as described above. The PCR products were analyzed in an agarose gel to identify the colonies containing the gene in the recombinant plasmid.

Figure 6:
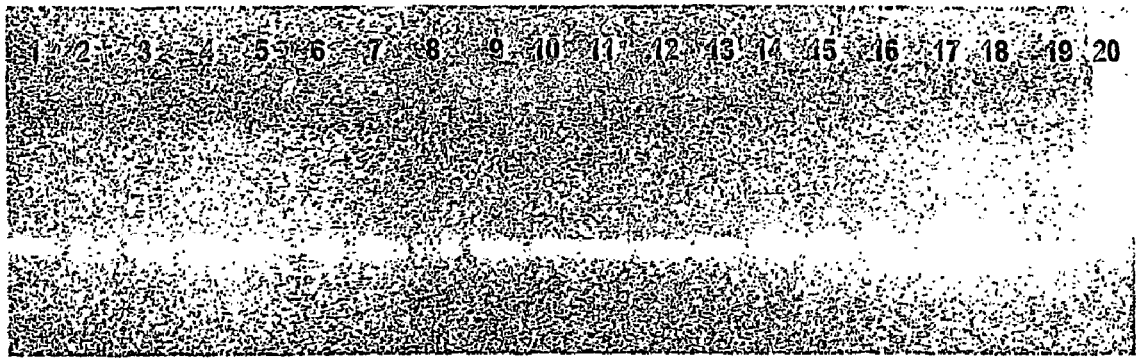
FIG. 6 is a gel photograph showing the PCR products from 19 selective positive colonies as well as a molecular marker.

The transformation resulted in several hundred white and few blue colonies. Nineteen randomly selected white colonies and 10 randomly selected blue colonies (not shown) were screened for pCR 2.1 TOPO/PNC-28EG. Colonies that contain pCR 2.1 TOPO/PNC-28EG were expected to show a fluorescent band of 62 bps. FIG. 6 shows the result of the analysis of the white colonies. FIG. 6 is a gel photograph showing amplified PCR products from PNC-28EG transformed white colonies. The PCR products from the 19 selected positive colonies were separated on a 2% agarose gel. Ethidium Bromide stained DNA bands migrated beyond the 100 bp mark (lane 20) indicating that the PCR products (1-18) are correct in size and that those colonies contain PNC-28EG/pCR 2.1 Topo.

Lane 19 (FIG. 6) shows a weak band below the expected size. Such a phenomenon usually occurs when the primers were not incorporated into a PCR product, which, in turn, suggests that there was no template (pCR 2.1 TOPO/PNC-28EG) present and that this PCR product is likely to be a false positive result.

Figure 7:
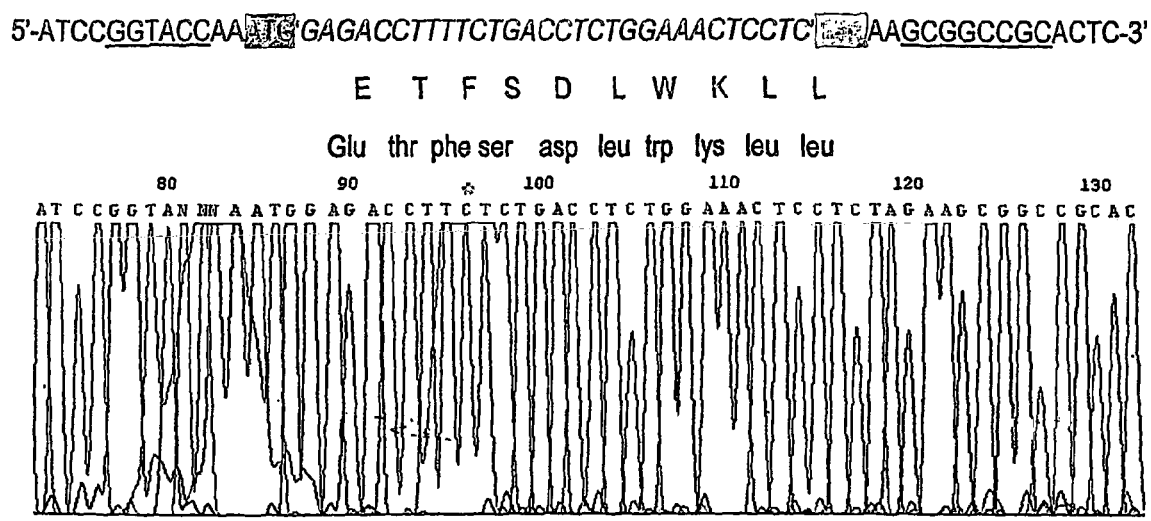
FIG. 7 shows the DNA sequence of Colony 8 from FIG. 6 as shown in SEQ. ID NO. 33. The top line is the actual DNA sequence and the bottom portion of the figure is a chromatogram generated from the automatic DNA sequence analysis. The amino acid sequences as encoded by the DNA of SEQ. ID NO. 33 is as shown in SEQ. ID NO. 34.

PCR amplification provided a means to screen for false positives among suspected positive colonies. This indicated, by the correct size of the insert, which colonies contained the recombinant plasmid. The plasmids of several of these colonies were subsequently sequenced to verify that PNC-28EG was inserted in the proper orientation and that there were no point mutations present in the sequence. Plasmids isolated from the colonies that corresponded to lanes 1, 5 and 8 (FIG. 6) were sent for automated DNA sequencing. Of the three plasmids, the one present in colony 8 (FIG. 6) contained the correct sequence for PNC-28EG. A comparison between the sequence obtained from colony 8 and the synthesized PNC-28EG sequence is shown in FIG. 7.

There is one point mutation present at position 96 (see star FIG. 7) in the segment that encodes for PNC-28. There is a change of base from T to C. This does not affect the identity of the amino acid sequence however, since the codon TTC also encodes the same amino acid as TTT, Phenylalanine. There are also three unknown nucleotides (N) present in the Kpn1 restriction site. This is most likely the result of an error produced by the automated sequencer. If these three nucleotides were to present a problem, Kpn1 would have been unable to cleave the restriction site and subsequent pAd/CMV/V5/PNC-28EG vector construction would be impossible. However Kpn I restriction remained unaffected and construction of the pAd/CMV/V5/PNC-28EG vector proceeded as described below.

Bacterial colony 8 was grown in liquid medium for 16 hrs, 37° C., when the bacteria were harvested and plasmid isolated as described above.

The next step in pAd/CMV/V5/PNC-28EG construction was cloning PNC-28EG into the entry vector, pENTR-11.

Figure 8:
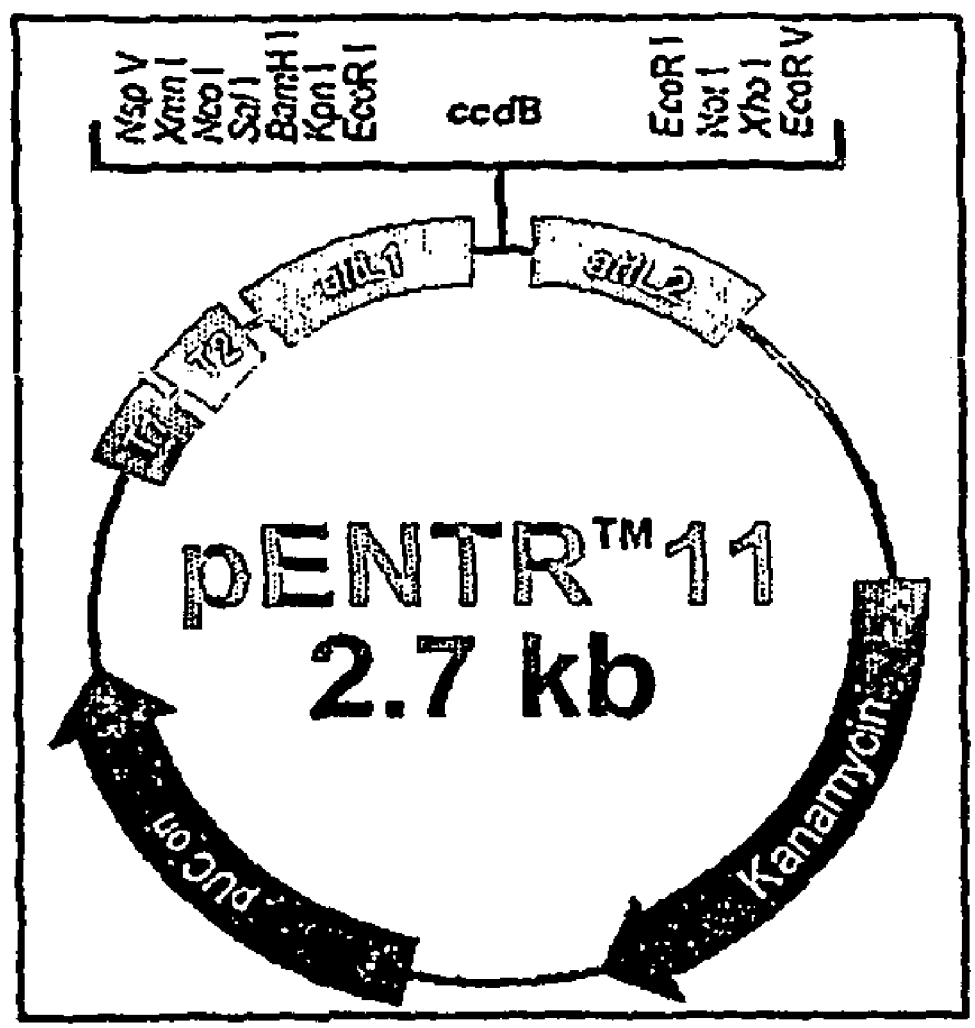
FIG. 8 is a map of the pENTR-11 vector.

FIG. 8 shows the vector map of pENTR-11. The entry vector contains recombination sites attL 1 and attL 2 that allow for the Recombinational cloning of PNC-28EG to the adenoviral expression vector, pAD/CMV/V5-DEST. It also contains a Kanamycin resistance gene, a ccdB gene between attL 1 and attL 2 as well as restriction sites for Kpn1 and Not1 in its multiple cloning site (MCS).

The ccdB gene found between the recombination sites of pENTR-11 allows for negative selection. The ccdB gene encodes for a protein that is toxic to TOP 10 *E. Coli* (the strain used) (Invitrogen). When PNC-28EG is cloned into the pENTR-11 vector the ccdb gene is removed. Therefore, colonies that do not contain PNC-28EG cannot grow. The Kanamycin resistance gene also allows for selection of positive colonies on Kanamycin treated culture plates.

The pENTR-11 vector was digested with Kpn1 and Not1 to expose protruding termini and allow the ligation of PNC-28EG. The digestion also results in the removal of the ccdB gene. pCR 2.1 TOPO/PNC-28EG was digested in the same manner. PNC-28EG was then purified from the pCR 2.1 Topo vector by separating the digested product on an agarose gel and excising the slab of agarose that contained the gene. The linearized pENTR11 vector was also purified in the same manner. The agarose slabs were melted and PNC-28EG was ligated to pENTR11 using T4 DNA ligase as the catalyst. The cloned entry vector, pENTR11/PNC-28EG, was used to transform chemically competent TOP 10 *E. coli* that were grown on selective kanamycin agarose plates.

Several dozen colonies grew and although they should all contain PNC-28EG, several colonies were subjected to PCR screening. The vector was digested with two different restriction enzymes to minimize the possibility that a vector not containing PNC-28EG could be ligated into a functional plasmid and produce false positives by circumvention of ccdB-selection. The DNA sequence of PNC-28EG itself should not be altered since the only reaction involved is a restriction reaction; no replication mechanisms were involved. This critical analysis showed that in fact not all colonies contained PNC-28EG. A PNC-28 positive clone was then grown in a large quantity and the recombinant entry vector, pENTR11/PNC-28EG, was isolated from this colony.

Figure 10:
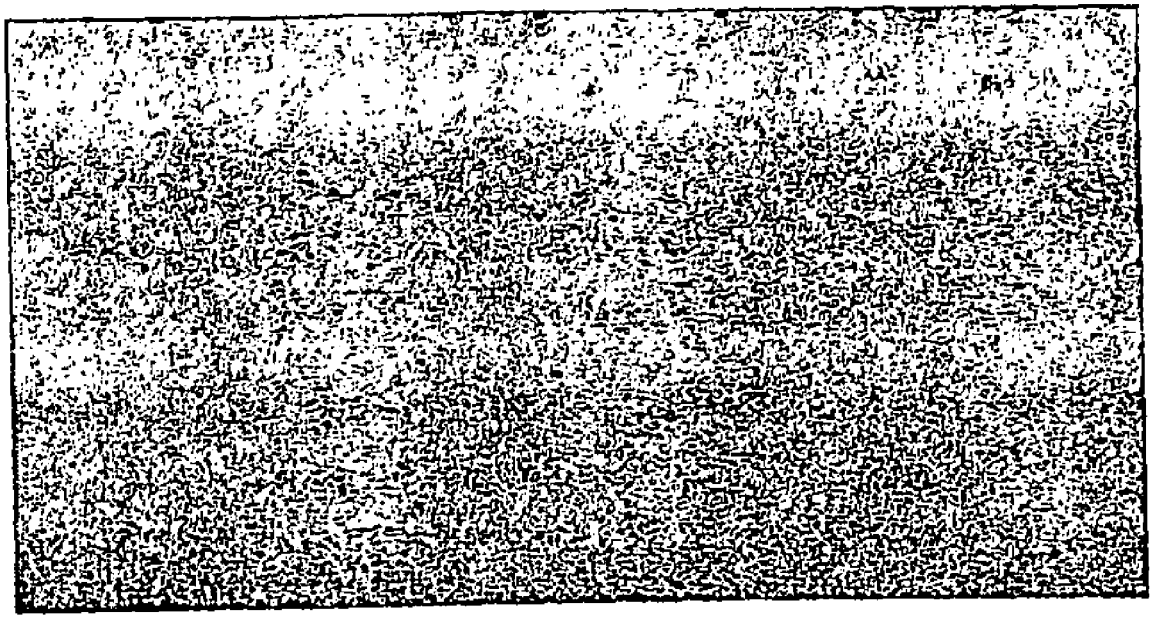
FIG. 10 is a gel photograph showing the PCR amplification products of PNC-28EG.
Figure 11:
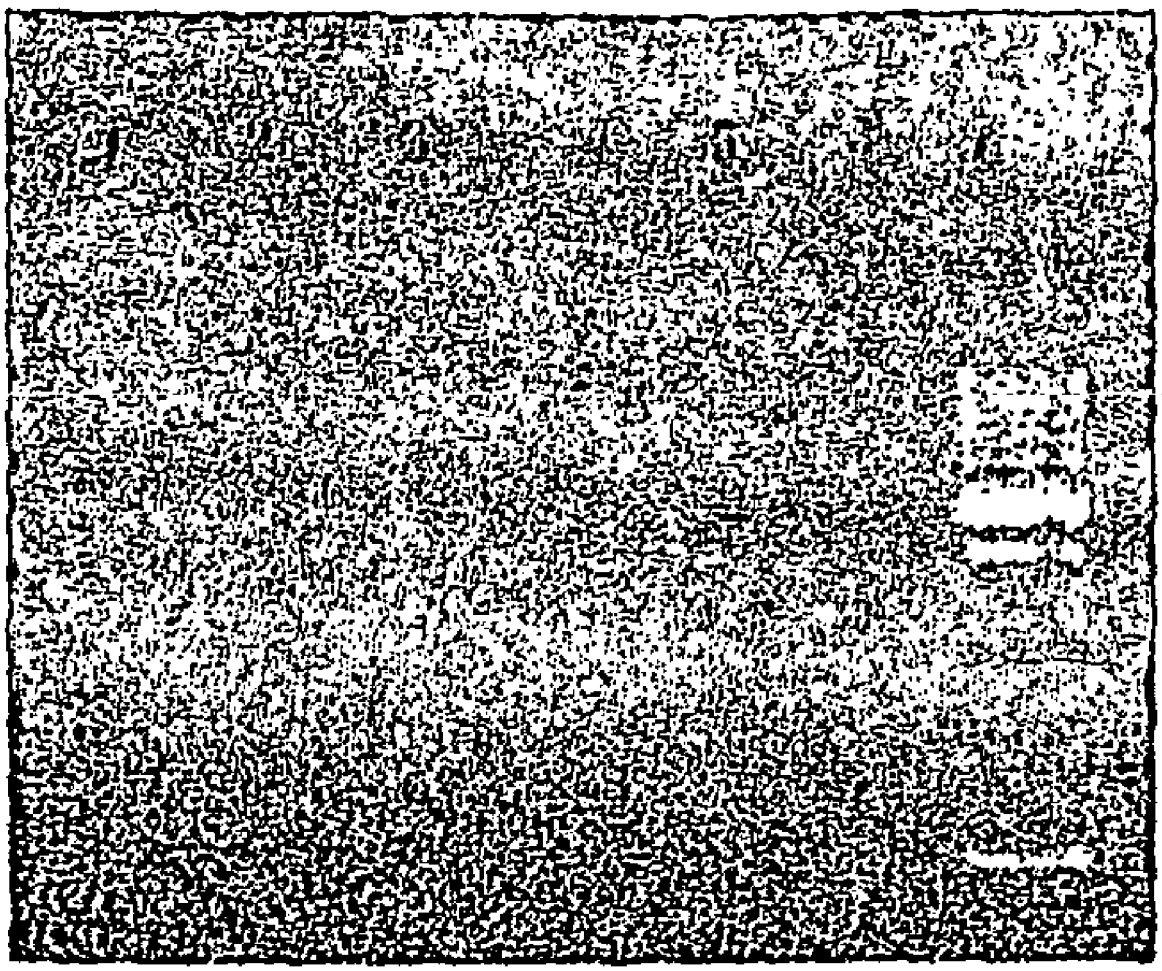
FIG. 11 is a gel photograph of purified pAd/CMV/V5/PNC-28EG (lanes 1 and 2) and 500 bp DNA marker (lane 7).

The final step in pAd/CMV/V5/PNC-28EG construction was subcloning PNC-28EG isolated from the pENTR11/PNC-28EG into pAD/CMV/V5-DEST, the adenoviral destination vector. pAD/CMV/V5-DEST contains attB1 and attB2 recombination sites that correspond to the attL 1 and attL 2 sites found on pENTR11. This allows for Integrase-mediated recombinant cloning of PNC-28EG from the pENTR-11 vector to pAD/CMV/V5-DEST. pAd/CMV/V5-DEST also contains a human cytomegalovirus (CMV) promoter that enhances the expression of PNC-28EG. Ampicillin resistance, ccdb negative selection and Herpes Simplex Virus Thymidine Kinase (TK) polyadenylation sequence for efficient transcription termination and polyadenylation of mRNA are also present in pAd/CMV/V5-DEST. FIG. 9 shows the recombination site of pAD/CMV/V5-DEST. pNC-28EG was cloned by recombination into pAD/CMVN5-DEST producing the desired expression clone.

pAD/CMV/V5/PNC-28EG that contained the necessary sequences encoding a replication incompetent virus able to express PNC-28. Chemically competent TOP 10 *E. Coli* were transformed with the pAd/CMV/V5/PNC-28EG vector and grown on selective ampicillin plates. Several dozen colonies grew and 10 randomly selected colonies were subjected to PCR screening (FIG. 10). FIG. 10 is a photograph showing the PCR products from the 10 selected positive colonies separated on a 2% agarose gel. Ethidium bromide stained DNA bands migrated beyond the 100 bp mark (lane 11), indicating that the PCR products (1-9) are correct in size and that those colonies contain pAD/CMV/V5/PNC-28EG. The weak band in lane 10 indicates a false positive colony. The migration of the bands thus indicated that 9 out of the 10 randomly selected colonies contain pAd/CMV/V5/PNC-28EG. These positive colonies were grown in large volumes of liquid culture and pAd/CMV/V5/PNC-28EG was purified from them. FIG. 11 shows the purified plasmid separated on an agarose gel.

The results of the gel indicate that the isolated pAd/CMV/V5/PNC-28EG is very pure. There are no other contaminants in the purified plasmid as there are only single bands in lanes 1 and 3. The molecular size of the band is approximately 35 kb.

Once pAd/CMV/V5/PNC-28EG was purified it was then used to transfect BMRPA1.TUC3 cells to verify that the gene for PNC-28 when transcribed and translated into the PNC-28 protein, is cytotoxic to pancreatic cancer cells and, therefore, that the constructed vector is useful as an anti-pancreatic cancer agent.

BMRPA1. TUC3 cells were seeded at a density of $1 \times 10^5$ cells in three wells of a 6-well plate with antibiotic free medium (cRMPI, 10% FBS). The cells were allowed to adhere to the wells through 4 hrs of incubation at 37° C. Two transfections were performed: the first well was transfected with pAD/CMV/V5/PNC-28EG and the second well with the control plasmid pAD/CMV/V5-GW/LacZ. In both cases the cells were transfected with 4 μg of plasmid and 10 μl of Lipofectamine 2000 (2:5 ratio). The cells in the third well served as a second control and received only Lipofectamine 2000 (10 μl).

Cells were returned to the incubator at 37° C. Twenty-four hours later the supernatant from each well was collected and counted for suspended cells. The viability of the cells was noted. The cells were replenished with fresh medium and returned to the incubator. This procedure was repeated with each successive 24 hrs until 72 hrs post transfection.

Figure 12A:
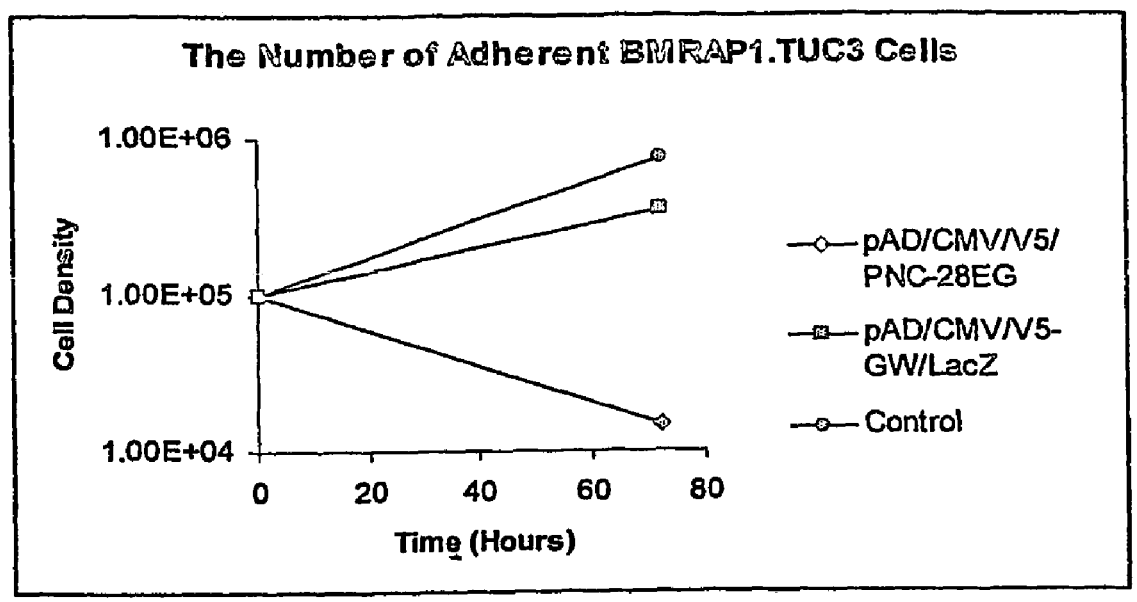
FIG. 12A graphically depicts the number of adherent BMRPA1.TUC3 cells 72 hours post transfection.

Seventy-two hours post transfection, the remaining adherent cells were then released and counted. FIG. 12A and Table 5 indicate the number of adherent cells in each respective well at 72 hrs. As shown in FIG. 12A and Table 5, cells transfected with pAD/CMV/V5/PNC-28EG show an 85% decrease in cell density from the initial seeding of cells. BMRPA1. TUC3 cells transfected with pAD/CMV/V5-GW/LacZ increased 3.5× fold 72 hours later and cells which were not transfected with any plasmid increased 7.5 fold from the initial amount of seeded cells. FIG. 12b shows the photography of the cells at 72 hours post transfection. Seventy two hours post transfection, the remaining adherent cells were then released and counted. As shown in FIG. 12b, seventy-two hours post transfection, 98% of the cells treated with pAD/CMV/V5/PNC-28EG were lysed compared to the control. Cells transfected with the LacZ vector and those with Lipofectamine 2000 only show 90-100% confluence.

TABLE 5

The Number of BMRPA1.TUC3 Cells Adherent after 72 hours Post Transfection

| Vector | Initial cell density | Remaining cell density 72 h post transfection |
|---|---|---|
| pAD/CMV/V5/PNC-28EG | $1.0 \times 10^5$ | $0.15 \times 10^5$ |
| pAD/CMV/V5-GW/LacZ | $1.0 \times 10^5$ | $3.5 \times 10^5$ |
| Lipofectamine 2000 (No plasmid) | $1.0 \times 10^5$ | $7.5 \times 10^5$ |

The >98% decrease of pancreatic carcinoma BMRPA1.TUC3 cells transfected by pAD/CMV/V5/PNC-28EG, while both control cell populations increase by 3.5 and 7.5 times above the starting number clearly indicates that the cytolytic effect in pAd/CMV/V5/PNC-28EG cells is due to the biosynthesis of PNC-28. BMRPA1.TUC3 cells transfected with the Ad/PNC-28EG vector also show the highest increase (5× control) in non-adherent and dead cells. In contrast, pAd/CMV/V5-GW/LacZ transfected BMRPA1.Tuc3 cells showed no cell lysis, and only a little slower growth when compared with Lipofectamine 2000 treated cells. The absence of cell lysis in pAd/CMV/V5-GW/LacZ transfected and Lipofectamine treated BMRPA1. TUC3 cells further strengthens the notion that newly synthesized PNC-28 protein is the cause of cell death in pAd/CMV/V5/PNC-28EG transfected cells. A rapid increase in non-adherent and dead cells in the pAd/CMV/V5/PNC-28EG transfected BMRPA1. TUC3 population 48 hrs post transfection, suggests that the expression of PNC-28 occurs within this time frame. This observation compares favorably with the time frame reported in Example II and FIG. 1 where PNC-28 attached to a penetratin sequence induced cell death upon BMRPA1. TUC3 cells within a 48-72 hr time period after exposure of the cells to the drug.

The foregoing specification, and the experimental results reported therein are illustrative and are not limitations of the scope of applicant's invention. Those skilled in the art will appreciate that various modifications can be made without departing from applicant's invention.

REFERENCES

1. Alberts, B., Johnson A., Lewis J., Raff M., Roberts K, Walter P. (2002). Molecular biology of the cell. Garland science.
2. Anderson, R. G. and Fletcher, J. C.; N. Engl. J. Med. 1980, 303: 1293-1297: Sounding boards. Gene therapy in human beings: When is it ethical to begin?
3. Bradu S (2000). An in vitro Model of Pancreatic Carcinogenesis: Characterization of transformation-associated biological and molecular alterations induced by the tobacco smoke carcinogen NNK in rat pancreatic BMRPA1 cells. PhD Thesis, School of Graduate Studies, SUNY-HSC at Brooklyn.
4. Bramson, J. L., Graham, F. L. and Gauldie, J.; Curr. Opin. Biotechnol. 1995, 6: 590-595: The use of adenoviral vectors for gene therapy and gene transfer in vivo.
5. Chen, Mack et al., 1997 "Persistance in muscle of an adenoviral vector that lacks all viral genes" Proc. Natl. Acad. Sci. USA 94(4):1414-1419.
6. Crouzet J, L. Naudin et al., 1997, "Recombinational construction in *Escherichia coli* of infectious adenoviral genomes" Proc. Natl. Acad. Sci. USA 94(4):1414-1419.
7. Douglas, J. T., Rogers, B. E., Rosenfeld, M. E., Michael, S. I., Feng, M. and Curiel, D. T.; Nat. Biotechnol. 1996, 14: 1574-1578: Targeted gene delivery by tropism-modified adenoviral vectors.
8. Goodbourn, S., Didcock, L. & Randall, R. E. (2000). Interferons: cell signaling, immune modulation, antiviral responses and virus countermeasures. *Journal of General Virology* 81, 2341-2365.
9. Graham F L, Smiley, J., Russel, W. C., and Narin, R. (1977). Characteristics of a Human Cell Line Transformed by DNA from Human Adenovirus Type 5. J. Gen. virol. 36, 59-74.

10. Gropp, R, Frye, M., Wagner, T. O. & Bargon, J. (1999). Epithelial defensins impair adenoviral infection: Implication for adenovirus-mediated gene therapy. *Gene Therapy* 10, 957-964.

11. Hitt, M. M., Addison, C. L. and Graham, F. L.; Adv. Pharmacol. 1996, 40: 137-206: Human adenovirus vectors for gene transfer into mammalian cells.

12. Invitrogen (2001) B-gal Staining Kit. Catalog No. K1465-01

13. Israel, B. F., Pickles, R. J., Segal, D. M., Gerard, R. D. and Kenney, S. C.; J. Virol. 2001, 75(11): 5215-5221: Enhancement of adenovirus vector entry into CD70-positive B-cell lines by using a bispecific CD70-adenovirus fiber antibody.

14. Kanovsky M, Raffo A, Drew L, Rosal R, Do T, Friedman F K, Rubinstein P, Visser J, Robinson R, Brandt-Rauf P W, Michl J, Fine R L, Pincus M R; Proc Natl Acad Sci USA. Oct. 23, 2001; 98(22):12438-43: Peptides from the amino terminal mdm-2-binding domain of p53, designed from conformational analysis, are selectively cytotoxic to transformed cells.

15. Kozarsky, K F and Wilson J M (1993). Gene Therapy: Adenovirus Vectros. Curr. Opin. Genet. Dev. 3, 499-503.

16. Krougliak V, and Graham F L (1995). Development of Cell Lines Capable of Complementing E1, E4, and Protein IX Defective Adenovirus Type 5 Mutants. Hum. Gene Ther. 6, 1575-1586.

17. Lusky, Christ et al., 1998 "In vitro and in vivo biology of recombinant adenovirus vectors with E1, E1/E2A, or E1/E4 deleted" *J. Virol.* 72(3):2022-3.

18. Mathias, P., Galleno, M. & Nemerow, G. R. (1998). Interactions of soluble recombinant integrin av β5 with human adenoviruses. Journal of General virology 75, 3365-3374.

19. Meredith, J. E., Jr, Winitz, S., Lewis, J. M., Hess, S., Ren, X. D., Renshaw, M. W. & Schwartz, M. A. (1996). The regulation of growth and intracellular signaling by integrins. *Endocrinology Reviews* 17, 207-220.

20. Michl J. D J Ohlbaum, S C Silverstein, 1976. 2-Deoxyglucose selectively inhibits Fc and complement receptor-mediated phagocytosis in mouse peritoneal macrophages. J Exp Med, 144: 1465-1483.

21. Morral, N., R. J. Parks, et al. (1998) "High doses of a helper-dependent adenoviral vector yield supraphysiological levels of alpha 1-antritrypsin with negligible toxicity." *Human Gene Therapy* 9(18):2709-2716.

22. Morral, O'Neal et al., 1999 "Administration of helper-dependent adenoviral vectors and sequential delivery of different vector serotype for long-term liver-directed gene transfer in baboons." *Proc. Natl. Acad. Sci. USA* 96(22): 12816-12821.

23. O'Neal, Zhou et al., 1998 "Toxicological comparison of E2a-deleted and first-generation adenoviral vectors expressing alpha1-antitrypsin after systemic delivery" *Human Gene Therapy* 9(11): 1597-98.

24. Russel, W. C. (2000) Update on adenovirus and its vectors. *Journal of General Virology*, Vol 81 2573-2604

25. Saiki, R. K., Scharf, S. J., Faloona, F., Mullis, K. B., Horn, G. T., Erlich, H. A. and Arnheim, N. (1985) Science, 230, 1350.

26. Sambrook, J., Fritsch, E. F. and Maniatis, T.; Molecular cloning. A laboratory manual. $2^{nd}$ ed. Cold Spring Harbor Laboratory Press 1989, Cold Spring Harbor, N.Y.

27. Schmiedl, A., Breitling, F. and Duebel, S.; Protein Engineering 2000, 13 (10): 725-734: Expression of a bispecific dsFv-dsFv' antibody fragment in *E. coli*.

28. Segal, D. M. and Bast, B. J. E. G.; J. E. Coligan, A. M. Kruisbeek, D. H. Marguiles, E. M. Shevach and W. Strober (ed), Current protocols in immunology. John Wiley & Sons, Inc, New York, N.Y. 1995, p. 12.13.11-12.13.16: Production of bispecific antibodies.

29. Stow, N. D., 1981, "Cloning a DNA fragment from the left-hand terminus of the adenovirus type 2 genome and its use in site-directed mutagenesis" *J. Virol.* 37:171-180.

30. Uchida T., Minei S., Gao, J., Wang C., Satoh T., Baba S. (2002) Clinical significance of p53, MDM2 and bcl-2 expression in transitional cell carcinoma of the bladder. Oncology Reports 9: 253-259.

31. Wang I. I. and Huang I. I. (2000) Adenovirus technology for gene manipulation and functional studies. *Drug Discovery Today* 5, 10-16.

32. Weitmann, S. D., Lark, R. H., Coney, L. R., Fort, D. W., Frasca V., Zurawski, V. R., Jr. and Kamen, B. A.; Cancer Res. 1992, 52: 3396-3401: Distribution of the folate receptor GP38 in normal and malignant cell lines and tissues.

33. Wickham, T. J., Segal, D. M., Roelvink, P. W., Carrion, M. E., Lizonova, A., Lee, G. M. and Kovesdi, I.; J. Virol. 1996, 70: 6831-6838: Targeted adenovirus gene transfer to endothelial and smooth muscle cells by using bispecific antibodies.

34. Yang, Y., Jooss, K. U., Su, Q., Ertl, H. C. J. and Wilson, J. M.; Gene Ther. 1996, 3: 137-144 Immune responses to viral antigens vs. transgene product in the elimination of recombinant adenovirus infected hepatocytes in vivo.

35. Yang, Y., Li, Q., Ertl, H. C. J. and Wilson, J. M.; J. Virol. 1995, 69: 2004-2015: Cellular and humoral immune responses to viral antigens create barriers to lung directed gene therapy with recombinant adenoviruses.

36. Yang, Y., Nunes, F. A., Berencsi, K., Furth, E. F., Gonczol, E. and Wilson, J. M.; Proc. Natl. Acad. Sci. 1994, 91: 4407-4411: Cellular immunity to viral antigens limits E1-deleted adenoviruses for gene therapy.

What is claimed is:

1. A replication incompetent Adenovirus (AdV) vector comprising a promoter sequence operably linked to a nucleotide sequence encoding a peptide, wherein the peptide consists of the amino acid sequence: PPLSQETFSDLWKLL (SEQ ID NO: 1), and wherein the E1 and E3 genes have been deleted.

2. A replication incompetent AdV vector comprising a promoter sequence operably linked to a nucleotide sequence encoding a peptide, wherein the peptide consists of the amino acid sequence: PPLSQETFS (SEQ ID NO: 2) and wherein the E1 and E3 genes have been deleted.

3. A replication incompetent AdV vector comprising a promoter sequence operably linked to a nucleotide sequence encoding a peptide, wherein the peptide consists of the amino acid sequence: ETFSDLWKLL (SEQ ID NO: 3) and wherein the E1 and E3 genes have been deleted.

4. The replication incompetent AdV vector of claim 3 wherein the nucleotide sequence consists of GAGACCTTTTCTGACCTCTGGAAACTCCTC (SEQ ID NO: 29).

5. The replication incompetent AdV vector of any of claim 1 or 2-4 wherein the promoter sequence is selected from the group consisting of: CMV, SV40, RSV, LTR, beta- actin, EF-1 alpha, Gal-Elb, UbC, beta-Casein, EM-7, EF, TEF1, CMV-2 and Bsd.

6. The replication incompetent AdV vector of claim 5 wherein the promoter sequence is CW.

* * * * *

SEQUENCE LISTING

```
<160> NUMBER OF SEQ ID NOS: 36

<210> SEQ ID NO 1
<211> LENGTH: 15
<212> TYPE: PRT
<213> ORGANISM: Artificial Sequence
<220> FEATURE:
<223> OTHER INFORMATION: peptide; amino acid residue 12-26 of human p53
      protein

<400> SEQUENCE: 1
```

```
Pro Pro Leu Ser Gln Glu Thr Phe Ser Asp Leu Trp Lys Leu Leu
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: peptide; amino acid residue 12-20 of human p53
      protein

<400> SEQUENCE: 2

Pro Pro Leu Ser Gln Glu Thr Phe Ser
1               5

<210> SEQ ID NO 3
<211> LENGTH: 10
<212> TYPE: PRT
<213> ORGANISM: Artificial Sequence
<220> FEATURE:
<223> OTHER INFORMATION: peptide; amino acid residue 17-26 of human p53
      protein

<400> SEQUENCE: 3

Glu Thr Phe Ser Asp Leu Trp Lys Leu Leu
1               5                   10

<210> SEQ ID NO 4
<211> LENGTH: 17
<212> TYPE: PRT
<213> ORGANISM: Artificial Sequence
<220> FEATURE:
<223> OTHER INFORMATION: peptide; penetration leader sequence from
      antennapedia

<400> SEQUENCE: 4

Lys Lys Trp Lys Met Arg Arg Asn Gln Phe Trp Val Lys Val Gln Arg
1               5                   10                  15

Gly

<210> SEQ ID NO 5
<211> LENGTH: 14
<212> TYPE: PRT
<213> ORGANISM: Artificial Sequence
<220> FEATURE:
<223> OTHER INFORMATION: peptide; HIV-1 TAT membrane penetrating leader
      sequence

<400> SEQUENCE: 5

Tyr Gly Arg Lys Lys Arg Arg Gln Arg Arg Pro Pro Gln
1               5                   10

<210> SEQ ID NO 6
<211> LENGTH: 13
<212> TYPE: PRT
<213> ORGANISM: Artificial Sequence
<220> FEATURE:
<223> OTHER INFORMATION: peptide; D-TAT membrane penetrating leader
      sequence

<400> SEQUENCE: 6

Gly Arg Lys Lys Arg Arg Gln Arg Arg Arg Pro Pro Gln
1               5                   10

<210> SEQ ID NO 7
<211> LENGTH: 13
```

```
<212> TYPE: PRT
<213> ORGANISM: Artificial Sequence
<220> FEATURE:
<223> OTHER INFORMATION: peptide; R-TAT membrane penetrating leader
      sequence

<400> SEQUENCE: 7

Gly Arg Arg Arg Arg Arg Arg Arg Arg Pro Pro Gln
1               5                   10

<210> SEQ ID NO 8
<211> LENGTH: 7
<212> TYPE: PRT
<213> ORGANISM: Artificial Sequence
<220> FEATURE:
<223> OTHER INFORMATION: peptide; SV40-NLS membrane penetrating leader
      sequence

<400> SEQUENCE: 8

Pro Lys Lys Lys Arg Lys Val
1               5

<210> SEQ ID NO 9
<211> LENGTH: 16
<212> TYPE: PRT
<213> ORGANISM: Artificial Sequence
<220> FEATURE:
<223> OTHER INFORMATION: peptide; HIV REV membrane penetrating leader
      sequence

<400> SEQUENCE: 9

Lys Arg Pro Ala Ala Ile Lys Lys Ala Gly Gln Ala Lys Lys Lys Lys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: peptide; HIV REV membrane penetrating leader
      sequence

<400> SEQUENCE: 10

Thr Arg Gln Ala Arg Arg Asn Arg Arg Arg Arg Trp Arg Glu Arg Gln
1               5                   10                  15

Arg

<210> SEQ ID NO 11
<211> LENGTH: 15
<212> TYPE: PRT
<213> ORGANISM: Artificial Sequence
<220> FEATURE:
<223> OTHER INFORMATION: peptide; FHV coat protein membrane penetrating
      leader sequence

<400> SEQUENCE: 11

Arg Arg Arg Arg Asn Arg Thr Arg Arg Asn Arg Arg Arg Val Arg
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: peptide; BMV GAG membrane penetrating leader
      sequence

<400> SEQUENCE: 12
```

Lys Met Thr Arg Ala Gln Arg Arg Ala Ala Arg Arg Asn Arg Trp
1               5                   10                  15

Thr Ala Arg

<210> SEQ ID NO 13
<211> LENGTH: 13
<212> TYPE: PRT
<213> ORGANISM: Artificial Sequence
<220> FEATURE:
<223> OTHER INFORMATION: peptide; HTLV-II REX membrane penetrating
      leader sequence

<400> SEQUENCE: 13

Thr Arg Arg Gln Arg Thr Arg Arg Ala Arg Arg Asn Arg
1               5                   10

<210> SEQ ID NO 14
<211> LENGTH: 19
<212> TYPE: PRT
<213> ORGANISM: Artificial Sequence
<220> FEATURE:
<223> OTHER INFORMATION: peptide; CCMV GAG membrane penetrating leader
      sequence

<400> SEQUENCE: 14

Lys Leu Thr Arg Ala Gln Arg Arg Ala Ala Ala Arg Lys Asn Lys Arg
1               5                   10                  15

Asn Thr Arg

<210> SEQ ID NO 15
<211> LENGTH: 17
<212> TYPE: PRT
<213> ORGANISM: Artificial Sequence
<220> FEATURE:
<223> OTHER INFORMATION: peptide; P22 N membrane penetrating leader
      sequence

<400> SEQUENCE: 15

Asn Ala Lys Thr Arg Arg His Glu Arg Arg Arg Lys Leu Ala Ile Glu
1               5                   10                  15

Arg

<210> SEQ ID NO 16
<211> LENGTH: 22
<212> TYPE: PRT
<213> ORGANISM: Artificial Sequence
<220> FEATURE:
<223> OTHER INFORMATION: peptide; LAMBDA N membrane penetrating leader
      sequence

<400> SEQUENCE: 16

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 17
<211> LENGTH: 18
<212> TYPE: PRT
<213> ORGANISM: Artificial Sequence
<220> FEATURE:
<223> OTHER INFORMATION: peptide; phi N membrane penetrating leader
      sequence

<400> SEQUENCE: 17

-continued

Thr Ala Lys Thr Arg Tyr Lys Ala Arg Arg Ala Glu Leu Ile Ala Glu
1               5                   10                  15

Arg Arg

<210> SEQ ID NO 18
<211> LENGTH: 16
<212> TYPE: PRT
<213> ORGANISM: Artificial Sequence
<220> FEATURE:
<223> OTHER INFORMATION: peptide; yeast PRPG membrane penetrating
      leader sequence

<400> SEQUENCE: 18

Thr Arg Arg Asn Lys Arg Asn Arg Ile Gln Glu Gln Leu Asn Arg Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: peptide; Human U2AF membrane penetrating leader
      sequence

<400> SEQUENCE: 19

Ser Gln Met Thr Arg Gln Ala Arg Arg Leu Tyr Val
1               5                   10

<210> SEQ ID NO 20
<211> LENGTH: 26
<212> TYPE: PRT
<213> ORGANISM: Artificial Sequence
<220> FEATURE:
<223> OTHER INFORMATION: peptide; Human C-FOS membrane penetrating
      leader sequence

<400> SEQUENCE: 20

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 21
<211> LENGTH: 28
<212> TYPE: PRT
<213> ORGANISM: Artificial Sequence
<220> FEATURE:
<223> OTHER INFORMATION: peptide; Human C-JUN membrane penetrating
      leader sequence

<400> SEQUENCE: 21

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 22
<211> LENGTH: 22
<212> TYPE: PRT
<213> ORGANISM: Artificial Sequence
<220> FEATURE:
<223> OTHER INFORMATION: peptide; Yeast GCN4 membrane penetrating leader
      sequence

<400> SEQUENCE: 22

-continued

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 23
<211> LENGTH: 18
<212> TYPE: PRT
<213> ORGANISM: Artificial Sequence
<220> FEATURE:
<223> OTHER INFORMATION: peptide; membrane penetrating leader sequence

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 18
<212> TYPE: PRT
<213> ORGANISM: Artificial Sequence
<220> FEATURE:
<223> OTHER INFORMATION: peptide; p-VEC membrane penetrating leader
      sequence

<400> SEQUENCE: 24

Leu Leu Ile Ile Leu Arg Arg Arg Ile Arg Lys Gln Ala Lys Ala His
1               5                   10                  15

Ser Lys

<210> SEQ ID NO 25
<211> LENGTH: 13
<212> TYPE: PRT
<213> ORGANISM: Artificial Sequence
<220> FEATURE:
<223> OTHER INFORMATION: peptide; used as a control

<400> SEQUENCE: 25

Met Pro Phe Ser Thr Gly Lys Arg Ile Met Leu Gly Glu
1               5                   10

<210> SEQ ID NO 26
<211> LENGTH: 21
<212> TYPE: DNA
<213> ORGANISM: Artificial Sequence
<220> FEATURE:
<223> OTHER INFORMATION: primer; PNC-283G-Rev

<400> SEQUENCE: 26
gagtgcggcc gcttctagag g                                          21

<210> SEQ ID NO 27
<211> LENGTH: 21
<212> TYPE: DNA
<213> ORGANISM: Artificial Sequence
<220> FEATURE:
<223> OTHER INFORMATION: primer; PNC-28Eg-Frw

<400> SEQUENCE: 27
atccggtacc aaatggagac c                                          21

<210> SEQ ID NO 28
<211> LENGTH: 30
<212> TYPE: DNA
<213> ORGANISM: Artificial Sequence

```
<220> FEATURE:
<223> OTHER INFORMATION: coding sequence for peptide of SEQ ID NO:3

<400> SEQUENCE: 28 gagaccttttt ctgacctctg gaaactcctc                                         30

<210> SEQ ID NO 29
<211> LENGTH: 30
<212> TYPE: DNA
<213> ORGANISM: Artificial Sequence
<220> FEATURE:
<223> OTHER INFORMATION: primer; nucleotide sequence

<400> SEQUENCE: 29 gagaccttttt ctgacctctg gaaactcctc                                         30

<210> SEQ ID NO 30
<211> LENGTH: 59
<212> TYPE: DNA
<213> ORGANISM: Artificial Sequence
<220> FEATURE:
<223> OTHER INFORMATION: primer; nucleotide sequence of PNC-28EG

<400> SEQUENCE: 30
atccggtacc aaatggagac cttttctgac ctctggaaac tcctcaagcg gccgcactc          59

<210> SEQ ID NO 31
<211> LENGTH: 10
<212> TYPE: PRT
<213> ORGANISM: Artificial Sequence
<220> FEATURE:
<223> OTHER INFORMATION: An amino acid sequence of a portion of SEQ ID
      NO:30

<400> SEQUENCE: 31

Glu Thr Phe Ser Asp Leu Trp Lys Leu Leu
1               5                   10

<210> SEQ ID NO 32
<211> LENGTH: 222
<212> TYPE: DNA
<213> ORGANISM: Artificial Sequence
<220> FEATURE:
<223> OTHER INFORMATION: primer; nucleotide sequence and restriction map
      of the pCR2-1

<400> SEQUENCE: 32
caggaaacag ctatgaccat gattacgcca agcttggtac cgagctcgga tccactagta         60
acggccgcca gtgtgctgga attcgccctt aagggcgaat tctgcagata tccatcacac        120
tggcggccgc tcgagcatgc atctagaggg cccaattcgc cctatagtga gtcgtattac        180
aattcactgg ccgtcgtttt acaacgtcgt cactgggaaa ac                           222

<210> SEQ ID NO 33
<211> LENGTH: 59
<212> TYPE: DNA
<213> ORGANISM: Artificial Sequence
<220> FEATURE:
<223> OTHER INFORMATION: primer; nucleotide sequence of Colony 8

<400> SEQUENCE: 33
atccggtacc aaatggagac cttttctgac ctctggaaac tcctcaagcg gccgcactc          59

<210> SEQ ID NO 34
<211> LENGTH: 10
```

```
<212> TYPE: PRT
<213> ORGANISM: Artificial Sequence
<220> FEATURE:
<223> OTHER INFORMATION: An amino acid sequence of a portion of SEQ ID
      NO:33

<400> SEQUENCE: 34

Glu Thr Phe Ser Asp Leu Trp Lys Leu Leu
1               5                   10

<210> SEQ ID NO 35
<211> LENGTH: 307
<212> TYPE: DNA
<213> ORGANISM: Artificial Sequence
<220> FEATURE:
<223> OTHER INFORMATION: primer; a nucleotide sequence
<220> FEATURE:
<221> NAME/KEY: misc_feature
<222> LOCATION: (172)..(173)
<223> OTHER INFORMATION: n is a, c, g, or t
<220> FEATURE:
<221> NAME/KEY: CDS
<222> LOCATION: (176)..(274)

<400> SEQUENCE: 35
ttgacgcaaa tgggcggtag gcgtgtacgg tgggaggtct atataagcag agctctctgg        60
ctaactagag aacccactgc ttactggctt atcgaaatta atacgactca ctataggag        120 acccaagctg gctagttaag ctatcaacaa gtttgtacaa aaaagcaggc tnnac cca        178
                                                             Pro
                                                             1 gct ttc ttg tac aaa gtg gtt gat cta gag ggc ccg cgg ttc gaa ggt        226
Ala Phe Leu Tyr Lys Val Val Asp Leu Glu Gly Pro Arg Phe Glu Gly
            5                   10                  15 aag cct atc cct aac cct ctc ctc ggt ctc gat tct acg cgt acc ggt        274
Lys Pro Ile Pro Asn Pro Leu Leu Gly Leu Asp Ser Thr Arg Thr Gly
        20                  25                  30 tagtaatgag tttaaacggg ggaggctaac tga                                    307

<210> SEQ ID NO 36
<211> LENGTH: 33
<212> TYPE: PRT
<213> ORGANISM: Artificial Sequence
<220> FEATURE:
<223> OTHER INFORMATION: Synthetic Construct

<400> SEQUENCE: 36

Pro Ala Phe Leu Tyr Lys Val Val Asp Leu Glu Gly Pro Arg Phe Glu
1               5                   10                  15

Gly Lys Pro Ile Pro Asn Pro Leu Leu Gly Leu Asp Ser Thr Arg Thr
            20                  25                  30

Gly
```